US 8,591,560 B2

(12) United States Patent  (10) Patent No.: US 8,591,560 B2
Jackson  (45) Date of Patent: Nov. 26, 2013

(54) DYNAMIC STABILIZATION CONNECTING MEMBER WITH ELASTIC CORE AND OUTER SLEEVE

(76) Inventor: Roger P. Jackson, Prairie Village, KS (US)

(*) Notice: Subject to any disclaimer, the term of this patent is extended or adjusted under 35 U.S.C. 154(b) by 0 days.

(21) Appl. No.: 13/507,853

(22) Filed: Aug. 2, 2012

(65) Prior Publication Data

US 2012/0303075 A1  Nov. 29, 2012

Related U.S. Application Data

(63) Continuation of application No. 11/894,001, filed on Aug. 17, 2007, now Pat. No. 8,292,926, and a continuation-in-part of application No. 11/522,503, filed on Sep. 14, 2006, now Pat. No. 7,766,915.

(60) Provisional application No. 60/851,353, filed on Oct. 12, 2006, provisional application No. 60/905,472, filed on Mar. 7, 2007, provisional application No. 60/722,300, filed on Sep. 30, 2005, provisional application No. 60/725,445, filed on Oct. 11, 2005, provisional application No. 60/728,912, filed on Oct. 21, 2005, provisional application No. 60/736,112, filed on Nov. 10, 2005, provisional application No. 60/832,644, filed on Jul. 21, 2006.

(51) Int. Cl.
*A61B 17/84* (2006.01)

(52) U.S. Cl.
USPC ............................................. 606/328

(58) Field of Classification Search
USPC ....... 606/246, 328, 86 A, 250, 254, 278, 279, 606/266, 301, 305, 308, 302, 326, 916
See application file for complete search history.

(56) References Cited

U.S. PATENT DOCUMENTS

| 854,956 A | 5/1907 | Martin |
| 2,243,717 A | 5/1941 | Moreira |
| 2,346,346 A | 4/1944 | Anderson |
| 2,362,999 A | 11/1944 | Elmer |
| 2,531,892 A | 11/1950 | Reese |
| 2,813,450 A | 11/1957 | Dzus |
| 3,013,244 A | 12/1961 | Rudy |
| 3,236,275 A | 2/1966 | Smith |

(Continued)

FOREIGN PATENT DOCUMENTS

| CA | 2577436 | 6/2006 |
| DE | 9202745.8 | 4/1992 |

(Continued)

OTHER PUBLICATIONS

Brochure of Sofamor Danek the Spine Specialist, TSRH, Pedicle Screw Spinal System, Publication Date: Jan. 23, 1995.

(Continued)

*Primary Examiner* — Pedro Philogene
(74) *Attorney, Agent, or Firm* — John C. McMahon (57) ABSTRACT

A dynamic fixation medical implant having at least two bone anchors includes a longitudinal connecting member assembly having an elongate core and an outer sleeve. The core is of one-piece construction, elastic, and includes end portions for attachment to the bone anchors. The outer sleeve may include compression grooves. The sleeve surrounds the core and extends between the pair of bone anchors, the sleeve being compressible between the bone anchors.

9 Claims, 4 Drawing Sheets

(56) References Cited

U.S. PATENT DOCUMENTS

| | | | |
|---|---|---|---|
| 3,604,487 A | 9/1971 | Gilbert | |
| 3,640,416 A | 2/1972 | Temple | |
| 4,033,139 A | 7/1977 | Frederick | |
| 4,041,939 A | 8/1977 | Hall | |
| 4,190,091 A | 2/1980 | Colognori | |
| 4,373,754 A | 2/1983 | Bollfrass et al. | |
| 4,448,191 A | 5/1984 | Rodnyansky et al. | |
| 4,484,570 A | 11/1984 | Sutter et al. | |
| 4,600,224 A | 7/1986 | Blose | |
| 4,611,581 A | 9/1986 | Steffee | |
| 4,653,486 A | 3/1987 | Coker | |
| 4,703,954 A | 11/1987 | Ortloff et al. | |
| 4,707,001 A | 11/1987 | Johnson | |
| 4,743,260 A | 5/1988 | Burton | |
| 4,748,260 A | 5/1988 | Marlett | |
| 4,759,672 A | 7/1988 | Nilsen et al. | |
| 4,790,297 A | 12/1988 | Luque | |
| 4,836,196 A | 6/1989 | Park et al. | |
| 4,877,020 A | 10/1989 | Vich | |
| 4,887,596 A | 12/1989 | Sherman | |
| 4,946,458 A | 8/1990 | Harms et al. | |
| 4,950,269 A | 8/1990 | Gaines, Jr. | |
| 5,005,562 A | 4/1991 | Cotrel | |
| 5,019,080 A | 5/1991 | Hemer | |
| 5,020,519 A | 6/1991 | Hayes et al. | |
| 5,022,791 A | 6/1991 | Isler | |
| 5,034,011 A | 7/1991 | Howland | |
| 5,067,955 A | 11/1991 | Cotrel | |
| 5,084,048 A | 1/1992 | Jacob et al. | |
| 5,092,635 A | 3/1992 | DeLange et al. | |
| 5,092,866 A | 3/1992 | Breard et al. | |
| 5,102,412 A | 4/1992 | Rogozinski | |
| 5,129,388 A | 7/1992 | Vignaud et al. | |
| 5,147,363 A | 9/1992 | Harle | |
| 5,154,719 A | 10/1992 | Cotrel | |
| 5,176,483 A | 1/1993 | Baumann et al. | |
| 5,176,678 A | 1/1993 | Tsou | |
| 5,176,680 A | 1/1993 | Vignaud et al. | |
| 5,180,393 A | 1/1993 | Commarmond | |
| 5,207,678 A | 5/1993 | Harms et al. | |
| 5,217,497 A | 6/1993 | Mehdian | |
| 5,257,993 A | 11/1993 | Asher et al. | |
| 5,261,907 A | 11/1993 | Vignaud et al. | |
| 5,261,912 A | 11/1993 | Frigg | |
| 5,275,601 A | 1/1994 | Gogolewski et al. | |
| 5,282,862 A | 2/1994 | Baker et al. | |
| 5,282,863 A | 2/1994 | Burton | |
| D346,217 S | 4/1994 | Sparker et al. | |
| 5,306,275 A | 4/1994 | Bryan | |
| 5,312,404 A | 5/1994 | Asher et al. | |
| 5,321,901 A | 6/1994 | Kelly | |
| 5,330,472 A | 7/1994 | Metz-Stavenhagen | |
| 5,346,493 A | 9/1994 | Stahurski et al. | |
| 5,358,289 A | 10/1994 | Banker et al. | |
| 5,360,431 A | 11/1994 | Puno et al. | |
| 5,375,823 A | 12/1994 | Navas | |
| 5,385,583 A | 1/1995 | Cotrel | |
| 5,395,371 A | 3/1995 | Miller et al. | |
| 5,409,489 A | 4/1995 | Sioufi | |
| 5,414,661 A | 5/1995 | Holmes | |
| 5,415,661 A | 5/1995 | Holmes | |
| 5,423,816 A | 6/1995 | Lin | |
| 5,427,418 A | 6/1995 | Watts | |
| 5,429,639 A | 7/1995 | Judet | |
| 5,443,467 A | 8/1995 | Biedermann et al. | |
| 5,466,237 A | 11/1995 | Byrd, III et al. | |
| 5,468,241 A | 11/1995 | Metz-Stavenhagen et al. | |
| 5,474,555 A | 12/1995 | Puno et al. | |
| 5,476,462 A | 12/1995 | Allard et al. | |
| 5,476,464 A | 12/1995 | Metz-Stavenhagen et al. | |
| 5,480,401 A | 1/1996 | Navas | |
| 5,484,437 A | 1/1996 | Michelson | |
| 5,484,440 A | 1/1996 | Allard | |
| 5,487,742 A | 1/1996 | Cotrel | |
| 5,489,307 A | 2/1996 | Kuslich et al. | |
| 5,490,750 A | 2/1996 | Gundy | |
| 5,496,321 A | 3/1996 | Puno et al. | |
| 5,499,892 A | 3/1996 | Reed | |
| 5,507,745 A | 4/1996 | Logroscino et al. | |
| 5,540,688 A | 7/1996 | Navas | |
| 5,545,165 A | 8/1996 | Biedermann et al. | |
| 5,554,157 A | 9/1996 | Errico et al. | |
| 5,562,660 A | 10/1996 | Grob | |
| 5,562,663 A | 10/1996 | Wisnewski et al. | |
| 5,569,247 A | 10/1996 | Morrison | |
| 5,569,251 A | 10/1996 | Baker et al. | |
| 5,584,834 A | 12/1996 | Errico et al. | |
| 5,586,984 A | 12/1996 | Errico et al. | |
| 5,591,166 A | 1/1997 | Bernhardt et al. | |
| 5,601,553 A | 2/1997 | Trebing et al. | |
| 5,607,304 A | 3/1997 | Bailey et al. | |
| 5,607,425 A | 3/1997 | Rogozinski | |
| 5,607,426 A | 3/1997 | Ralph et al. | |
| 5,607,428 A | 3/1997 | Lin | |
| 5,611,800 A | 3/1997 | Davis et al. | |
| 5,628,740 A | 5/1997 | Mullane | |
| 5,630,817 A | 5/1997 | Rokegem | |
| 5,641,256 A | 6/1997 | Gundy | |
| 5,643,260 A | 7/1997 | Doherty | |
| 5,643,261 A | 7/1997 | Schafer et al. | |
| 5,647,873 A | 7/1997 | Errico et al. | |
| 5,662,652 A | 9/1997 | Schafer et al. | |
| 5,662,653 A | 9/1997 | Songer et al. | |
| 5,669,909 A | 9/1997 | Zdeblick et al. | |
| 5,669,911 A | 9/1997 | Errico et al. | |
| 5,672,175 A * | 9/1997 | Martin | 606/86 A |
| 5,672,176 A | 9/1997 | Biedermann et al. | |
| 5,676,703 A | 10/1997 | Gelbard | |
| 5,681,319 A | 10/1997 | Biedermann et al. | |
| 5,683,390 A | 11/1997 | Metz-Stavenhagen et al. | |
| 5,690,630 A | 11/1997 | Errico et al. | |
| 5,697,929 A | 12/1997 | Mellinger | |
| 5,711,709 A | 1/1998 | McCoy | |
| 5,713,898 A | 2/1998 | Stucker et al. | |
| 5,716,356 A | 2/1998 | Biedermann et al. | |
| 5,720,751 A | 2/1998 | Jackson | |
| 5,723,013 A | 3/1998 | Jeanson et al. | |
| 5,725,527 A | 3/1998 | Biedermann et al. | |
| 5,725,528 A | 3/1998 | Errico et al. | |
| 5,728,098 A | 3/1998 | Sherman et al. | |
| 5,733,286 A | 3/1998 | Errico et al. | |
| 5,738,685 A | 4/1998 | Halm et al. | |
| 5,741,254 A | 4/1998 | Henry et al. | |
| 5,752,957 A | 5/1998 | Ralph et al. | |
| 5,782,830 A | 7/1998 | Farris | |
| 5,782,833 A | 7/1998 | Haider | |
| 5,792,044 A | 8/1998 | Foley et al. | |
| 5,797,911 A | 8/1998 | Sherman et al. | |
| 5,800,435 A | 9/1998 | Errico et al. | |
| 5,800,547 A | 9/1998 | Schafer et al. | |
| 5,810,816 A | 9/1998 | Roussouly et al. | |
| 5,817,094 A | 10/1998 | Errico et al. | |
| 5,863,293 A | 1/1999 | Richelsoph | |
| 5,873,878 A | 2/1999 | Harms et al. | |
| 5,876,402 A | 3/1999 | Errico et al. | |
| 5,879,350 A | 3/1999 | Sherman et al. | |
| 5,879,351 A | 3/1999 | Viart | |
| 5,882,350 A | 3/1999 | Ralph et al. | |
| 5,885,286 A | 3/1999 | Sherman et al. | |
| 5,891,145 A | 4/1999 | Morrison et al. | |
| 5,902,231 A | 5/1999 | Foley et al. | |
| RE36,221 E | 6/1999 | Breard et al. | |
| 5,910,141 A | 6/1999 | Morrison et al. | |
| 5,938,663 A | 8/1999 | Petreto | |
| 5,944,465 A | 8/1999 | Janitzki | |
| 5,951,553 A | 9/1999 | Betz | |
| 5,954,725 A | 9/1999 | Sherman et al. | |
| 5,961,517 A | 10/1999 | Biedermann et al. | |
| 5,964,760 A | 10/1999 | Richelsoph | |
| 6,001,098 A | 12/1999 | Metz-Stavenhagen et al. | |
| 6,004,349 A | 12/1999 | Jackson | |
| 6,010,503 A | 1/2000 | Richelsoph et al. | |
| 6,019,759 A | 2/2000 | Rogozinski | |
| 6,022,350 A | 2/2000 | Ganem | |

(56) References Cited

U.S. PATENT DOCUMENTS

| | | |
|---|---|---|
| 6,053,917 A | 4/2000 | Sherman et al. |
| 6,059,786 A | 5/2000 | Jackson |
| 6,063,090 A | 5/2000 | Schlapfer |
| 6,074,391 A | 6/2000 | Metz-Stavenhagen et al. |
| 6,077,262 A | 6/2000 | Schlapfer et al. |
| 6,086,588 A | 7/2000 | Ameil et al. |
| 6,090,110 A | 7/2000 | Metz-Stavenhagen |
| 6,090,111 A | 7/2000 | Nichols |
| 6,099,528 A | 8/2000 | Saurat |
| 6,102,912 A | 8/2000 | Cazin et al. |
| 6,102,913 A | 8/2000 | Jackson |
| 6,110,172 A | 8/2000 | Jackson |
| 6,113,601 A | 9/2000 | Tatar |
| 6,117,137 A | 9/2000 | Halm et al. |
| 6,132,431 A | 10/2000 | Nilsson et al. |
| 6,132,432 A | 10/2000 | Richelsoph |
| 6,132,434 A | 10/2000 | Sherman et al. |
| 6,136,002 A | 10/2000 | Shih et al. |
| 6,139,549 A | 10/2000 | Keller |
| 6,143,032 A | 11/2000 | Schafer et al. |
| 6,146,383 A | 11/2000 | Studer et al. |
| 6,183,472 B1 | 2/2001 | Lutz |
| 6,186,718 B1 | 2/2001 | Fogard |
| 6,187,005 B1 | 2/2001 | Brace et al. |
| 6,193,720 B1 | 2/2001 | Yuan et al. |
| 6,214,012 B1 | 4/2001 | Karpman et al. |
| RE37,161 E | 5/2001 | Michelson et al. |
| 6,224,596 B1 | 5/2001 | Jackson |
| 6,224,598 B1 | 5/2001 | Jackson |
| 6,235,028 B1 | 5/2001 | Brumfield et al. |
| 6,235,034 B1 | 5/2001 | Bray |
| 6,241,730 B1 | 6/2001 | Alby |
| 6,248,105 B1 | 6/2001 | Schlapfer et al. |
| 6,248,107 B1 | 6/2001 | Foley et al. |
| 6,251,112 B1 | 6/2001 | Jackson |
| 6,254,146 B1 | 7/2001 | Church |
| 6,254,602 B1 | 7/2001 | Justis |
| 6,267,764 B1 | 7/2001 | Elberg |
| 6,267,765 B1 | 7/2001 | Taylor et al. |
| 6,273,888 B1 | 8/2001 | Justis |
| 6,277,122 B1 | 8/2001 | McGahan et al. |
| 6,280,442 B1 | 8/2001 | Barker et al. |
| 6,280,445 B1 | 8/2001 | Morrison et al. |
| 6,287,308 B1 | 9/2001 | Betz et al. |
| 6,287,311 B1 | 9/2001 | Sherman et al. |
| 6,290,700 B1 | 9/2001 | Schmotzer |
| 6,296,642 B1 | 10/2001 | Morrison et al. |
| 6,296,643 B1 | 10/2001 | Hopf et al. |
| 6,299,613 B1 | 10/2001 | Ogilvie et al. |
| 6,302,888 B1 | 10/2001 | Mellinger et al. |
| 6,309,391 B1 | 10/2001 | Crandall et al. |
| 6,309,394 B1 | 10/2001 | Staehlin et al. |
| 6,315,564 B1 | 11/2001 | Levisman |
| 6,315,779 B1 | 11/2001 | Morrison et al. |
| 6,331,179 B1 | 12/2001 | Freid et al. |
| 6,355,040 B1 | 3/2002 | Richelsoph et al. |
| RE37,665 E | 4/2002 | Ralph et al. |
| 6,368,321 B1 | 4/2002 | Jackson |
| 6,371,957 B1 | 4/2002 | Amrein et al. |
| 6,402,752 B2 | 6/2002 | Schaffler-Wachter et al. |
| 6,402,757 B1 | 6/2002 | Moore et al. |
| 6,440,133 B1 | 8/2002 | Beale et al. |
| 6,440,137 B1 | 8/2002 | Horvath et al. |
| 6,443,956 B1 | 9/2002 | Ray |
| 6,451,021 B1 | 9/2002 | Ralph et al. |
| 6,471,703 B1 | 10/2002 | Ashman |
| 6,471,705 B1 | 10/2002 | Biedermann et al. |
| 6,478,801 B1 | 11/2002 | Ralph et al. |
| 6,485,491 B1 | 11/2002 | Farris et al. |
| 6,485,492 B1 | 11/2002 | Halm et al. |
| 6,485,494 B1 | 11/2002 | Haider |
| 6,488,681 B2 | 12/2002 | Martin et al. |
| 6,508,818 B2 | 1/2003 | Steiner et al. |
| 6,511,484 B2 | 1/2003 | Torode et al. |
| 6,520,962 B1 | 2/2003 | Taylor et al. |
| 6,527,804 B1 | 3/2003 | Gauchet et al. |
| 6,530,929 B1 | 3/2003 | Justis et al. |
| 6,533,786 B1 | 3/2003 | Needham et al. |
| 6,539,826 B2 | 4/2003 | Oesterle et al. |
| 6,540,749 B2 | 4/2003 | Schafer et al. |
| 6,547,790 B2 | 4/2003 | Harkey, III et al. |
| 6,551,320 B2 | 4/2003 | Lieberman |
| 6,551,323 B2 | 4/2003 | Doubler et al. |
| 6,554,831 B1 | 4/2003 | Rivard et al. |
| 6,554,832 B2 | 4/2003 | Shluzas |
| 6,554,834 B1 | 4/2003 | Crozet et al. |
| 6,558,387 B2 | 5/2003 | Errico et al. |
| 6,562,038 B1 | 5/2003 | Morrison |
| 6,562,040 B1 | 5/2003 | Wagner |
| 6,565,565 B1 | 5/2003 | Yuan et al. |
| 6,565,567 B1 | 5/2003 | Haider |
| 6,582,436 B2 | 6/2003 | Schlapfer et al. |
| 6,582,466 B1 | 6/2003 | Gauchet |
| 6,585,740 B2 | 7/2003 | Schlapfer et al. |
| 6,595,992 B1 | 7/2003 | Wagner et al. |
| 6,595,993 B2 | 7/2003 | Donno et al. |
| 6,599,294 B2 | 7/2003 | Fuss et al. |
| 6,610,063 B2 | 8/2003 | Kumar et al. |
| 6,613,050 B1 | 9/2003 | Wagner et al. |
| 6,616,667 B1 | 9/2003 | Steiger et al. |
| 6,616,669 B2 | 9/2003 | Ogilvie |
| 6,623,485 B2 | 9/2003 | Doubler et al. |
| 6,626,347 B2 | 9/2003 | Ng |
| 6,626,907 B2 | 9/2003 | Campbell et al. |
| 6,626,908 B2 | 9/2003 | Cooper et al. |
| 6,635,059 B2 | 10/2003 | Randall et al. |
| 6,635,060 B2 | 10/2003 | Hanson et al. |
| 6,648,885 B1 | 11/2003 | Friesem |
| 6,648,887 B2 | 11/2003 | Ashman |
| 6,648,888 B1 | 11/2003 | Shluzas |
| 6,652,526 B1 | 11/2003 | Arafiles |
| 6,652,765 B1 | 11/2003 | Beaty |
| 6,656,179 B1 | 12/2003 | Schaefer et al. |
| 6,656,181 B2 | 12/2003 | Dixon et al. |
| 6,660,004 B2 | 12/2003 | Barker et al. |
| 6,660,006 B2 | 12/2003 | Markworth et al. |
| 6,663,632 B1 | 12/2003 | Frigg |
| 6,663,635 B2 | 12/2003 | Frigg et al. |
| 6,673,073 B1 | 1/2004 | Schafer |
| 6,676,661 B1 | 1/2004 | Martin Benlloch |
| 6,679,833 B2 | 1/2004 | Smith et al. |
| 6,682,529 B2 | 1/2004 | Stahurski |
| 6,682,530 B2 | 1/2004 | Dixon et al. |
| 6,689,133 B2 | 2/2004 | Morrison et al. |
| 6,689,134 B2 | 2/2004 | Ralph et al. |
| 6,695,843 B2 | 2/2004 | Biedermann et al. |
| 6,695,851 B2 | 2/2004 | Zdeblick et al. |
| 6,699,249 B2 | 3/2004 | Schlapfer et al. |
| 6,706,045 B2 | 3/2004 | Lin et al. |
| 6,712,818 B1 | 3/2004 | Michelson |
| 6,716,213 B2 | 4/2004 | Shitoto |
| 6,716,214 B1 | 4/2004 | Jackson |
| 6,716,247 B2 | 4/2004 | Michelson |
| 6,723,100 B2 | 4/2004 | Biedermann et al. |
| 6,730,093 B2 | 5/2004 | Saint Martin |
| 6,730,127 B2 | 5/2004 | Michelson |
| 6,733,502 B2 | 5/2004 | Altarac et al. |
| 6,736,816 B2 | 5/2004 | Ritland |
| 6,736,820 B2 | 5/2004 | Biedermann et al. |
| 6,740,086 B2 | 5/2004 | Richelsoph |
| 6,743,231 B1 | 6/2004 | Gray et al. |
| 6,746,449 B2 | 6/2004 | Jones et al. |
| 6,755,829 B1 | 6/2004 | Bono et al. |
| 6,755,835 B2 | 6/2004 | Schultheiss et al. |
| 6,755,836 B1 | 6/2004 | Lewis |
| 6,761,723 B2 | 7/2004 | Buttermann et al. |
| 6,767,351 B2 | 7/2004 | Orbay et al. |
| 6,770,075 B2 | 8/2004 | Howland |
| 6,778,861 B1 | 8/2004 | Liebrecht et al. |
| 6,780,186 B2 | 8/2004 | Errico et al. |
| 6,783,527 B2 | 8/2004 | Drewry et al. |
| 6,790,209 B2 | 9/2004 | Beale et al. |
| 6,802,844 B2 | 10/2004 | Ferree |
| 6,827,719 B2 | 12/2004 | Ralph et al. |

(56) References Cited

U.S. PATENT DOCUMENTS

| | | |
|---|---|---|
| 6,830,571 B2 | 12/2004 | Lenke et al. |
| 6,835,196 B2 | 12/2004 | Biedermann et al. |
| 6,837,889 B2 | 1/2005 | Shluzas |
| 6,840,940 B2 | 1/2005 | Ralph et al. |
| 6,843,791 B2 | 1/2005 | Serhan |
| 6,858,031 B2 | 2/2005 | Morrison et al. |
| 6,869,432 B2 | 3/2005 | Schlapfer et al. |
| 6,869,433 B2 | 3/2005 | Glascott |
| 6,872,208 B1 | 3/2005 | McBride et al. |
| 6,896,676 B2 | 5/2005 | Zubok et al. |
| 6,896,677 B1 | 5/2005 | Lin |
| 6,932,817 B2 | 8/2005 | Baynham et al. |
| 6,932,820 B2 | 8/2005 | Osman |
| 6,945,972 B2 | 9/2005 | Frigg et al. |
| 6,953,462 B2 | 10/2005 | Liebermann |
| 6,955,677 B2 | 10/2005 | Dahners |
| 6,958,065 B2 | 10/2005 | Ueyama et al. |
| 6,964,664 B2 | 11/2005 | Freid et al. |
| 6,964,665 B2 | 11/2005 | Thomas et al. |
| 6,964,667 B2 | 11/2005 | Shaolian et al. |
| 6,966,910 B2 | 11/2005 | Ritland |
| 6,974,460 B2 | 12/2005 | Carbone et al. |
| 6,979,334 B2 | 12/2005 | Dalton |
| 6,981,973 B2 | 1/2006 | McKinley |
| 6,986,771 B2 | 1/2006 | Paul et al. |
| 6,989,011 B2 | 1/2006 | Paul et al. |
| 6,991,632 B2 | 1/2006 | Ritland |
| 7,004,947 B2 | 2/2006 | Shluzas et al. |
| RE39,035 E | 3/2006 | Finn et al. |
| 7,008,422 B2 | 3/2006 | Foley et al. |
| 7,008,424 B2 | 3/2006 | Teitelbaum |
| 7,011,660 B2 | 3/2006 | Sherman et al. |
| 7,018,378 B2 | 3/2006 | Biedermann et al. |
| 7,018,379 B2 | 3/2006 | Drewry et al. |
| 7,022,122 B2 | 4/2006 | Amrein et al. |
| 7,029,475 B2 | 4/2006 | Panjabi |
| RE39,089 E | 5/2006 | Ralph et al. |
| 7,052,497 B2 | 5/2006 | Sherman et al. |
| 7,056,321 B2 | 6/2006 | Pagliuca et al. |
| 7,066,062 B2 | 6/2006 | Flesher |
| 7,066,937 B2 | 6/2006 | Shluzas |
| 7,081,116 B1 | 7/2006 | Carly |
| 7,083,621 B2 | 8/2006 | Shaolian et al. |
| 7,087,057 B2 | 8/2006 | Konieczynski et al. |
| 7,090,674 B2 | 8/2006 | Doubler et al. |
| 7,090,679 B2 | 8/2006 | Saint-Martin et al. |
| 7,090,680 B2 | 8/2006 | Bonati et al. |
| 7,094,242 B2 | 8/2006 | Ralph et al. |
| 7,118,576 B2 | 10/2006 | Gitis et al. |
| 7,121,755 B2 | 10/2006 | Schlapfer et al. |
| 7,125,410 B2 | 10/2006 | Freudiger |
| 7,125,426 B2 | 10/2006 | Moumene et al. |
| 7,128,743 B2 | 10/2006 | Metz-Stavenhagen |
| 7,137,985 B2 | 11/2006 | Jahng |
| 7,141,051 B2 | 11/2006 | Janowski et al. |
| 7,144,396 B2 | 12/2006 | Shluzas |
| 7,163,538 B2 | 1/2007 | Altarac et al. |
| 7,163,539 B2 | 1/2007 | Abdelgany et al. |
| 7,166,108 B2 | 1/2007 | Mazda et al. |
| 7,179,261 B2 | 2/2007 | Sicvol et al. |
| 7,186,255 B2 | 3/2007 | Baynham et al. |
| 7,188,626 B2 | 3/2007 | Foley et al. |
| 7,207,991 B2 | 4/2007 | Michelson |
| 7,207,992 B2 | 4/2007 | Ritland |
| 7,211,085 B2 | 5/2007 | Michelson |
| 7,211,086 B2 | 5/2007 | Biedermann et al. |
| 7,211,087 B2 | 5/2007 | Young |
| 7,214,227 B2 | 5/2007 | Colleran et al. |
| 7,223,268 B2 | 5/2007 | Biedermann |
| 7,229,441 B2 | 6/2007 | Trieu et al. |
| 7,264,621 B2 | 9/2007 | Coates et al. |
| 7,270,665 B2 | 9/2007 | Morrison et al. |
| 7,282,064 B2 | 10/2007 | Chin |
| 7,291,151 B2 | 11/2007 | Alvarez |
| 7,291,153 B2 | 11/2007 | Glascott |
| 7,294,127 B2 | 11/2007 | Hawkins et al. |
| 7,294,128 B2 | 11/2007 | Alleyne et al. |
| 7,294,129 B2 | 11/2007 | Hawkins et al. |
| 7,306,603 B2 | 12/2007 | Boehm, Jr. et al. |
| 7,306,604 B2 | 12/2007 | Carli |
| 7,306,606 B2 | 12/2007 | Sasing |
| 7,314,467 B2 | 1/2008 | Howland |
| 7,316,684 B1 | 1/2008 | Baccelli et al. |
| 7,322,979 B2 | 1/2008 | Crandall et al. |
| 7,329,258 B2 | 2/2008 | Studer |
| 7,335,201 B2 | 2/2008 | Doubler et al. |
| 7,335,202 B2 | 2/2008 | Matthis et al. |
| 7,338,490 B2 | 3/2008 | Ogilvie et al. |
| 7,338,491 B2 | 3/2008 | Baker et al. |
| 7,361,196 B2 | 4/2008 | Fallin et al. |
| 7,377,921 B2 | 5/2008 | Studer et al. |
| 7,476,238 B2 | 1/2009 | Panjabi |
| 7,491,208 B2 | 2/2009 | Pond, Jr. et al. |
| 7,556,639 B2 | 7/2009 | Rothman et al. |
| 7,559,942 B2 | 7/2009 | Paul et al. |
| 7,563,274 B2 | 7/2009 | Justis et al. |
| 7,563,283 B2 | 7/2009 | Kwak |
| 7,588,589 B2 | 9/2009 | Falahee |
| 7,601,166 B2 | 10/2009 | Biedermann et al. |
| 7,604,653 B2 | 10/2009 | Kitchen |
| 7,604,654 B2 | 10/2009 | Fallin et al. |
| 7,611,518 B2 * | 11/2009 | Walder et al. ............... 606/86 A |
| 7,615,068 B2 | 11/2009 | Timm et al. |
| 7,618,444 B2 * | 11/2009 | Shluzas ...................... 606/279 |
| 7,621,912 B2 * | 11/2009 | Harms et al. .................... 606/59 |
| 7,621,940 B2 | 11/2009 | Harms et al. |
| 7,625,393 B2 | 12/2009 | Fallin et al. |
| 7,632,292 B2 | 12/2009 | Sengupta et al. |
| 7,641,673 B2 | 1/2010 | LeCouedic et al. |
| 7,651,515 B2 | 1/2010 | Mack et al. |
| 7,655,026 B2 | 2/2010 | Justis et al. |
| 7,658,739 B2 | 2/2010 | Shluzas |
| 7,658,752 B2 | 2/2010 | Labrom et al. |
| 7,682,375 B2 | 3/2010 | Ritland |
| 7,695,496 B2 | 4/2010 | Labrom et al. |
| 7,695,498 B2 | 4/2010 | Ritland |
| 7,695,514 B2 | 4/2010 | Kwak |
| 7,713,288 B2 | 5/2010 | Timm et al. |
| 7,722,649 B2 * | 5/2010 | Biedermann et al. ......... 606/257 |
| 7,763,048 B2 | 7/2010 | Fortin et al. |
| 7,763,052 B2 | 7/2010 | Jahng |
| 7,766,941 B2 | 8/2010 | Paul |
| 7,766,942 B2 | 8/2010 | Patterson et al. |
| 7,766,943 B1 | 8/2010 | Fallin et al. |
| 7,776,071 B2 | 8/2010 | Fortin et al. |
| 7,776,075 B2 | 8/2010 | Bruneau et al. |
| 7,785,349 B2 | 8/2010 | Walder et al. |
| 7,785,350 B2 | 8/2010 | Eckhardt et al. |
| 7,785,351 B2 | 8/2010 | Gordon et al. |
| 7,794,480 B2 | 9/2010 | Gordon et al. |
| 7,806,913 B2 | 10/2010 | Fanger et al. |
| 7,811,309 B2 | 10/2010 | Timm et al. |
| 7,815,663 B2 | 10/2010 | Trieu |
| 7,815,664 B2 | 10/2010 | Sherman et al. |
| 7,828,823 B2 | 11/2010 | Rogeau et al. |
| 7,850,715 B2 | 12/2010 | Banouskou et al. |
| 7,875,059 B2 | 1/2011 | Patterson et al. |
| 2001/0001119 A1 | 5/2001 | Lombardo |
| 2001/0023350 A1 | 9/2001 | Choi |
| 2001/0037111 A1 | 11/2001 | Dixon et al. |
| 2002/0007184 A1 | 1/2002 | Ogilvie et al. |
| 2002/0013586 A1 | 1/2002 | Justis et al. |
| 2002/0035366 A1 | 3/2002 | Walder et al. |
| 2002/0045898 A1 | 4/2002 | Freid et al. |
| 2002/0058942 A1 | 5/2002 | Biedermann et al. |
| 2002/0068975 A1 | 6/2002 | Teitelbaum et al. |
| 2002/0072751 A1 | 6/2002 | Jackson |
| 2002/0077701 A1 | 6/2002 | Kuslich |
| 2002/0082602 A1 | 6/2002 | Biedermann et al. |
| 2002/0095153 A1 | 7/2002 | Jones et al. |
| 2002/0111626 A1 | 8/2002 | Ralph et al. |
| 2002/0133159 A1 | 9/2002 | Jackson |
| 2002/0143341 A1 | 10/2002 | Biedermann et al. |
| 2002/0173789 A1 | 11/2002 | Howland |

(56) References Cited

U.S. PATENT DOCUMENTS

| | | |
|---|---|---|
| 2002/0193795 A1 | 12/2002 | Gertzbein et al. |
| 2003/0023240 A1 | 1/2003 | Amrein et al. |
| 2003/0023243 A1 | 1/2003 | Biedermann et al. |
| 2003/0073996 A1 | 4/2003 | Doubler et al. |
| 2003/0083657 A1 | 5/2003 | Drewry et al. |
| 2003/0093078 A1 | 5/2003 | Ritland |
| 2003/0100896 A1 | 5/2003 | Biedermann et al. |
| 2003/0105460 A1 | 6/2003 | Crandall et al. |
| 2003/0109880 A1 | 6/2003 | Shirado et al. |
| 2003/0114852 A1 | 6/2003 | Biedermann et al. |
| 2003/0125741 A1 | 7/2003 | Biedermann et al. |
| 2003/0149432 A1 | 8/2003 | Frigg et al. |
| 2003/0153911 A1 | 8/2003 | Shluzas |
| 2003/0163133 A1 | 8/2003 | Altarac et al. |
| 2003/0171749 A1 | 9/2003 | Le Couedic et al. |
| 2003/0176862 A1 | 9/2003 | Taylor et al. |
| 2003/0191470 A1 | 10/2003 | Ritland |
| 2003/0199873 A1 | 10/2003 | Richelsoph |
| 2003/0208203 A1 | 11/2003 | Lim et al. |
| 2003/0208204 A1 | 11/2003 | Bailey et al. |
| 2003/0212398 A1 | 11/2003 | Jackson |
| 2003/0216735 A1 | 11/2003 | Altarac et al. |
| 2003/0220642 A1 | 11/2003 | Freudiger |
| 2003/0220643 A1 | 11/2003 | Ferree |
| 2003/0225408 A1 | 12/2003 | Nichols et al. |
| 2004/0002708 A1 | 1/2004 | Ritland |
| 2004/0006342 A1 | 1/2004 | Altarac et al. |
| 2004/0049189 A1 | 3/2004 | Le Couedic et al. |
| 2004/0049190 A1 | 3/2004 | Biedermann et al. |
| 2004/0073215 A1 | 4/2004 | Carli |
| 2004/0078082 A1 | 4/2004 | Lange |
| 2004/0087949 A1 | 5/2004 | Bono et al. |
| 2004/0087952 A1 | 5/2004 | Borgstrom et al. |
| 2004/0092934 A1 | 5/2004 | Howland |
| 2004/0097933 A1 | 5/2004 | Lourdel et al. |
| 2004/0116929 A1 | 6/2004 | Barker et al. |
| 2004/0133207 A1 | 7/2004 | Abdou |
| 2004/0138662 A1 | 7/2004 | Landry et al. |
| 2004/0143265 A1 | 7/2004 | Landry et al. |
| 2004/0147928 A1 | 7/2004 | Landry et al. |
| 2004/0147929 A1 | 7/2004 | Biedermann et al. |
| 2004/0158247 A1 | 8/2004 | Sitiso et al. |
| 2004/0162560 A1 | 8/2004 | Raynor et al. |
| 2004/0172022 A1 | 9/2004 | Landry et al. |
| 2004/0172025 A1 | 9/2004 | Drewry et al. |
| 2004/0176766 A1 | 9/2004 | Shluzas |
| 2004/0186473 A1 | 9/2004 | Cournoyer et al. |
| 2004/0210216 A1 | 10/2004 | Farris et al. |
| 2004/0220567 A1 | 11/2004 | Eisermann et al. |
| 2004/0220671 A1 | 11/2004 | Ralph et al. |
| 2004/0225289 A1 | 11/2004 | Biedermann et al. |
| 2004/0236327 A1 | 11/2004 | Paul et al. |
| 2004/0236328 A1 | 11/2004 | Paul et al. |
| 2004/0236329 A1 | 11/2004 | Panjabi |
| 2004/0236330 A1 | 11/2004 | Purcell et al. |
| 2004/0249380 A1 | 12/2004 | Glascott |
| 2004/0260283 A1 | 12/2004 | Wu et al. |
| 2004/0267264 A1 | 12/2004 | Konieczynski et al. |
| 2005/0027296 A1 | 2/2005 | Thramann et al. |
| 2005/0033298 A1 | 2/2005 | Hawkes et al. |
| 2005/0038432 A1 | 2/2005 | Shaolian et al. |
| 2005/0049708 A1 | 3/2005 | Atkinson et al. |
| 2005/0055026 A1 | 3/2005 | Biedermann et al. |
| 2005/0065514 A1 | 3/2005 | Studer |
| 2005/0065515 A1 | 3/2005 | Jahng |
| 2005/0065516 A1 | 3/2005 | Jahng |
| 2005/0065517 A1 | 3/2005 | Chin |
| 2005/0070899 A1 | 3/2005 | Doubler et al. |
| 2005/0080415 A1 | 4/2005 | Keyer et al. |
| 2005/0085812 A1 | 4/2005 | Sherman |
| 2005/0085815 A1 | 4/2005 | Harms et al. |
| 2005/0085816 A1 | 4/2005 | Michelson |
| 2005/0096652 A1 | 5/2005 | Burton |
| 2005/0096654 A1 | 5/2005 | Lin |
| 2005/0107788 A1 | 5/2005 | Beaurain et al. |
| 2005/0113927 A1 | 5/2005 | Malek |
| 2005/0124991 A1 | 6/2005 | Jahng |
| 2005/0131404 A1 | 6/2005 | Mazda et al. |
| 2005/0131407 A1 | 6/2005 | Sicvol et al. |
| 2005/0131413 A1 | 6/2005 | O'Driscoll et al. |
| 2005/0137597 A1 | 6/2005 | Butler et al. |
| 2005/0143737 A1 | 6/2005 | Pafford et al. |
| 2005/0143823 A1 | 6/2005 | Boyd et al. |
| 2005/0149020 A1 | 7/2005 | Jahng |
| 2005/0149023 A1 | 7/2005 | Ritland |
| 2005/0154389 A1 | 7/2005 | Selover et al. |
| 2005/0154390 A1 | 7/2005 | Biedermann et al. |
| 2005/0154391 A1 | 7/2005 | Doherty et al. |
| 2005/0159750 A1 | 7/2005 | Doherty |
| 2005/0165396 A1 | 7/2005 | Fortin et al. |
| 2005/0165400 A1 | 7/2005 | Fernandez |
| 2005/0171540 A1 | 8/2005 | Lim et al. |
| 2005/0171543 A1 | 8/2005 | Timm et al. |
| 2005/0177157 A1 | 8/2005 | Jahng |
| 2005/0182401 A1 | 8/2005 | Timm et al. |
| 2005/0187548 A1 | 8/2005 | Butler et al. |
| 2005/0187555 A1 | 8/2005 | Biedermann et al. |
| 2005/0192580 A1 | 9/2005 | Dalton |
| 2005/0203511 A1 | 9/2005 | Wilson-MacDonald et al. |
| 2005/0203513 A1 | 9/2005 | Jahng et al. |
| 2005/0203514 A1 | 9/2005 | Jahng et al. |
| 2005/0203516 A1 | 9/2005 | Biedermann et al. |
| 2005/0203517 A1 | 9/2005 | Jahng et al. |
| 2005/0203518 A1 | 9/2005 | Biedermann et al. |
| 2005/0203519 A1 | 9/2005 | Harms et al. |
| 2005/0216001 A1 | 9/2005 | David |
| 2005/0216003 A1 | 9/2005 | Biedermann et al. |
| 2005/0228501 A1 | 10/2005 | Miller et al. |
| 2005/0234450 A1 | 10/2005 | Barker |
| 2005/0234451 A1 | 10/2005 | Markworth |
| 2005/0234452 A1 | 10/2005 | Malandain |
| 2005/0234453 A1 | 10/2005 | Shaolian et al. |
| 2005/0234454 A1 | 10/2005 | Chin |
| 2005/0234456 A1 | 10/2005 | Malandain |
| 2005/0240181 A1 | 10/2005 | Boomer et al. |
| 2005/0240183 A1 | 10/2005 | Vaughan |
| 2005/0245930 A1 | 11/2005 | Timm et al. |
| 2005/0251137 A1 | 11/2005 | Ball |
| 2005/0251140 A1 | 11/2005 | Shaolian et al. |
| 2005/0251141 A1 | 11/2005 | Frigg et al. |
| 2005/0261685 A1 | 11/2005 | Fortin et al. |
| 2005/0261687 A1 | 11/2005 | Garamszegi et al. |
| 2005/0267470 A1 | 12/2005 | McBride |
| 2005/0267471 A1 | 12/2005 | Biedermann et al. |
| 2005/0267474 A1 | 12/2005 | Dalton |
| 2005/0267477 A1 | 12/2005 | Jackson |
| 2005/0273099 A1 | 12/2005 | Baccelli et al. |
| 2005/0273101 A1 | 12/2005 | Schumacher |
| 2005/0277919 A1 | 12/2005 | Slivka et al. |
| 2005/0277922 A1 | 12/2005 | Trieu et al. |
| 2005/0277923 A1 | 12/2005 | Sweeney |
| 2005/0277925 A1 | 12/2005 | Mujwid |
| 2005/0277927 A1 | 12/2005 | Guenther et al. |
| 2005/0277928 A1 | 12/2005 | Boschert |
| 2005/0277931 A1 | 12/2005 | Sweeney et al. |
| 2005/0277934 A1 | 12/2005 | Vardiman |
| 2005/0283152 A1 | 12/2005 | Lindemann et al. |
| 2005/0283157 A1 | 12/2005 | Coates et al. |
| 2005/0283238 A1 | 12/2005 | Reiley |
| 2005/0283244 A1 | 12/2005 | Gordon et al. |
| 2005/0288669 A1 | 12/2005 | Abdou |
| 2005/0288670 A1 | 12/2005 | Panjabi |
| 2005/0288671 A1 | 12/2005 | Yuan et al. |
| 2005/0288672 A1 | 12/2005 | Ferree |
| 2005/0288673 A1 | 12/2005 | Catbagan et al. |
| 2006/0004357 A1 | 1/2006 | Lee et al. |
| 2006/0004359 A1 | 1/2006 | Kramer et al. |
| 2006/0004360 A1 | 1/2006 | Kramer et al. |
| 2006/0004363 A1 | 1/2006 | Brockmeyer et al. |
| 2006/0009767 A1 | 1/2006 | Kiester |
| 2006/0009768 A1 | 1/2006 | Ritland |
| 2006/0009769 A1 | 1/2006 | Lieberman |
| 2006/0009770 A1 | 1/2006 | Speirs et al. |
| 2006/0009775 A1 | 1/2006 | Dec et al. |

(56) References Cited

U.S. PATENT DOCUMENTS

| | | |
|---|---|---|
| 2006/0009780 A1 | 1/2006 | Foley et al. |
| 2006/0009846 A1 | 1/2006 | Trieu et al. |
| 2006/0015099 A1 | 1/2006 | Cannon et al. |
| 2006/0015104 A1 | 1/2006 | Dalton |
| 2006/0025767 A1 | 2/2006 | Khalili |
| 2006/0025768 A1 | 2/2006 | Iott et al. |
| 2006/0025770 A1 | 2/2006 | Schlapfer et al. |
| 2006/0030850 A1 | 2/2006 | Keegan et al. |
| 2006/0036240 A1 | 2/2006 | Colleran et al. |
| 2006/0036242 A1 | 2/2006 | Nilsson et al. |
| 2006/0036244 A1 | 2/2006 | Spitler et al. |
| 2006/0036246 A1 | 2/2006 | Carl et al. |
| 2006/0036252 A1 | 2/2006 | Baynham et al. |
| 2006/0036256 A1 | 2/2006 | Carl et al. |
| 2006/0036259 A1 | 2/2006 | Carl et al. |
| 2006/0036260 A1 | 2/2006 | Runco et al. |
| 2006/0036323 A1 | 2/2006 | Carl et al. |
| 2006/0036324 A1 | 2/2006 | Sachs et al. |
| 2006/0041259 A1 | 2/2006 | Paul et al. |
| 2006/0052780 A1 | 3/2006 | Errico et al. |
| 2006/0052783 A1 | 3/2006 | Dant et al. |
| 2006/0052784 A1 | 3/2006 | Dant et al. |
| 2006/0052786 A1 | 3/2006 | Dant et al. |
| 2006/0058788 A1 | 3/2006 | Hammer et al. |
| 2006/0058790 A1 | 3/2006 | Carl et al. |
| 2006/0064090 A1 | 3/2006 | Park |
| 2006/0064091 A1 | 3/2006 | Ludwig et al. |
| 2006/0064092 A1 | 3/2006 | Howland |
| 2006/0069390 A1 | 3/2006 | Frigg |
| 2006/0074419 A1 | 4/2006 | Taylor et al. |
| 2006/0079894 A1 | 4/2006 | Colleran et al. |
| 2006/0079895 A1 | 4/2006 | McLeer |
| 2006/0079896 A1 | 4/2006 | Kwak |
| 2006/0079898 A1 | 4/2006 | Ainsworth |
| 2006/0079899 A1 | 4/2006 | Ritland |
| 2006/0084977 A1 | 4/2006 | Liebermann |
| 2006/0084981 A1 | 4/2006 | Shluzas |
| 2006/0084982 A1 | 4/2006 | Kim |
| 2006/0084983 A1 | 4/2006 | Kim |
| 2006/0084984 A1 | 4/2006 | Kim |
| 2006/0084985 A1 | 4/2006 | Kim |
| 2006/0084987 A1 | 4/2006 | Kim |
| 2006/0084988 A1 | 4/2006 | Kim |
| 2006/0084989 A1 | 4/2006 | Dickinson et al. |
| 2006/0084991 A1 | 4/2006 | Borgstrom |
| 2006/0084993 A1 | 4/2006 | Landry et al. |
| 2006/0084995 A1 | 4/2006 | Biedermann et al. |
| 2006/0085069 A1 | 4/2006 | Kim |
| 2006/0089643 A1 | 4/2006 | Mujwid |
| 2006/0089644 A1 | 4/2006 | Felix |
| 2006/0095037 A1 | 5/2006 | Jones et al. |
| 2006/0106380 A1 | 5/2006 | Colleran et al. |
| 2006/0106381 A1 | 5/2006 | Ferree |
| 2006/0106383 A1 | 5/2006 | Biedermann et al. |
| 2006/0111714 A1 | 5/2006 | Foley |
| 2006/0116677 A1 | 6/2006 | Burd et al. |
| 2006/0122597 A1 | 6/2006 | Jojnes et al. |
| 2006/0122599 A1 | 6/2006 | Drewry |
| 2006/0129147 A1 | 6/2006 | Biedermann et al. |
| 2006/0129149 A1 | 6/2006 | Iott et al. |
| 2006/0129239 A1 | 6/2006 | Kwak |
| 2006/0142758 A1 | 6/2006 | Petit |
| 2006/0142760 A1 | 6/2006 | McDonnell |
| 2006/0142761 A1 | 6/2006 | Landry et al. |
| 2006/0149228 A1 | 7/2006 | Schlapfer |
| 2006/0149229 A1 | 7/2006 | Kwak |
| 2006/0149232 A1 | 7/2006 | Sasing |
| 2006/0149238 A1 | 7/2006 | Sherman et al. |
| 2006/0149241 A1 | 7/2006 | Richelsoph et al. |
| 2006/0149244 A1 | 7/2006 | Amrein et al. |
| 2006/0155277 A1 | 7/2006 | Metz-Stavenhagen |
| 2006/0155278 A1 | 7/2006 | Warnick |
| 2006/0161152 A1 | 7/2006 | Ensign et al. |
| 2006/0167454 A1 | 7/2006 | Ludwig et al. |
| 2006/0167455 A1 | 7/2006 | Clement et al. |
| 2006/0173454 A1 | 8/2006 | Spitler et al. |
| 2006/0173456 A1 | 8/2006 | Hawkes et al. |
| 2006/0184171 A1 | 8/2006 | Biedermann |
| 2006/0184180 A1 | 8/2006 | Augostino |
| 2006/0189984 A1 | 8/2006 | Fallin |
| 2006/0189985 A1 | 8/2006 | Lewis |
| 2006/0195090 A1* | 8/2006 | Suddaby .................. 606/61 |
| 2006/0195093 A1 | 8/2006 | Jahng |
| 2006/0195198 A1 | 8/2006 | Schumacher |
| 2006/0200123 A1 | 9/2006 | Mueller |
| 2006/0200130 A1 | 9/2006 | Hawkins |
| 2006/0200131 A1 | 9/2006 | Chao et al. |
| 2006/0200132 A1 | 9/2006 | Chao et al. |
| 2006/0200135 A1 | 9/2006 | Sherman et al. |
| 2006/0200138 A1 | 9/2006 | Michelson |
| 2006/0200139 A1 | 9/2006 | Michelson |
| 2006/0200149 A1 | 9/2006 | Hoy et al. |
| 2006/0210494 A1 | 9/2006 | Rabiei et al. |
| 2006/0212033 A1 | 9/2006 | Rothman |
| 2006/0212034 A1 | 9/2006 | Triplett et al. |
| 2006/0217713 A1 | 9/2006 | Serhan et al. |
| 2006/0217714 A1 | 9/2006 | Serhan et al. |
| 2006/0217715 A1 | 9/2006 | Albert et al. |
| 2006/0217716 A1 | 9/2006 | Baker et al. |
| 2006/0229608 A1 | 10/2006 | Foster |
| 2006/0229609 A1 | 10/2006 | Wang |
| 2006/0229612 A1 | 10/2006 | Rothman |
| 2006/0229613 A1 | 10/2006 | Timm |
| 2006/0229614 A1 | 10/2006 | Foley et al. |
| 2006/0229615 A1 | 10/2006 | Abdou |
| 2006/0235389 A1 | 10/2006 | Albert et al. |
| 2006/0235392 A1 | 10/2006 | Hammer et al. |
| 2006/0235393 A1 | 10/2006 | Bono et al. |
| 2006/0241593 A1 | 10/2006 | Sherman et al. |
| 2006/0241595 A1 | 10/2006 | Molz, IV et al. |
| 2006/0241600 A1 | 10/2006 | Ensign et al. |
| 2006/0241769 A1 | 10/2006 | Gordon |
| 2006/0241771 A1 | 10/2006 | Gordon |
| 2006/0247624 A1 | 11/2006 | Banouskou et al. |
| 2006/0247630 A1 | 11/2006 | Iott et al. |
| 2006/0247631 A1 | 11/2006 | Ahn et al. |
| 2006/0247632 A1 | 11/2006 | Winslow |
| 2006/0247633 A1 | 11/2006 | Winslow |
| 2006/0247635 A1 | 11/2006 | Gordon |
| 2006/0247636 A1 | 11/2006 | Yuan et al. |
| 2006/0247637 A1 | 11/2006 | Colleran |
| 2006/0247779 A1 | 11/2006 | Gordon |
| 2006/0264933 A1 | 11/2006 | Baker et al. |
| 2006/0264934 A1 | 11/2006 | Fallin |
| 2006/0264935 A1 | 11/2006 | White |
| 2006/0264936 A1 | 11/2006 | Partin et al. |
| 2006/0264937 A1 | 11/2006 | White |
| 2006/0264940 A1 | 11/2006 | Hartmannt |
| 2006/0264942 A1 | 11/2006 | Lim et al. |
| 2006/0264962 A1 | 11/2006 | Chin et al. |
| 2006/0269940 A1 | 11/2006 | Harman |
| 2006/0276787 A1 | 12/2006 | Zubok et al. |
| 2006/0276791 A1 | 12/2006 | Shluzas |
| 2006/0276792 A1 | 12/2006 | Ensign et al. |
| 2006/0282074 A1 | 12/2006 | Renaud et al. |
| 2006/0282075 A1 | 12/2006 | Labrom |
| 2006/0282076 A1 | 12/2006 | Labrom |
| 2006/0282077 A1 | 12/2006 | Labrom |
| 2006/0282078 A1 | 12/2006 | Labrom |
| 2006/0282079 A1 | 12/2006 | Labrom |
| 2006/0282080 A1 | 12/2006 | Albert |
| 2006/0293657 A1 | 12/2006 | Hartmann |
| 2006/0293659 A1 | 12/2006 | Alvarez |
| 2006/0293663 A1 | 12/2006 | Walkenhorst |
| 2006/0293665 A1 | 12/2006 | Shluzas |
| 2006/0293666 A1 | 12/2006 | Matthis et al. |
| 2007/0005062 A1 | 1/2007 | Lange |
| 2007/0005063 A1 | 1/2007 | Bruneau |
| 2007/0005137 A1 | 1/2007 | Kwak |
| 2007/0016188 A1 | 1/2007 | Boehm, Jr. et al. |
| 2007/0016190 A1 | 1/2007 | Martinez |
| 2007/0016193 A1 | 1/2007 | Ritland |
| 2007/0016194 A1 | 1/2007 | Shaolian et al. |
| 2007/0016198 A1 | 1/2007 | Boehm, Jr. et al. |

(56) References Cited

U.S. PATENT DOCUMENTS

| | | |
|---|---|---|
| 2007/0016199 A1 | 1/2007 | Boehm, Jr. et al. |
| 2007/0021750 A1 | 1/2007 | Shluzas et al. |
| 2007/0043355 A1 | 2/2007 | Bette et al. |
| 2007/0043356 A1 | 2/2007 | Timm |
| 2007/0043357 A1 | 2/2007 | Kirschman |
| 2007/0043358 A1 | 2/2007 | Molz, IV et al. |
| 2007/0043359 A1 | 2/2007 | Altarac et al. |
| 2007/0043364 A1 | 2/2007 | Cawley et al. |
| 2007/0049931 A1 | 3/2007 | Justis et al. |
| 2007/0049933 A1 | 3/2007 | Ahn et al. |
| 2007/0049936 A1 | 3/2007 | Colleran |
| 2007/0055235 A1 | 3/2007 | Janowski et al. |
| 2007/0055236 A1 | 3/2007 | Hudgins |
| 2007/0055238 A1 | 3/2007 | Biedermann et al. |
| 2007/0055239 A1 | 3/2007 | Sweeney et al. |
| 2007/0055240 A1 | 3/2007 | Matthis et al. |
| 2007/0055241 A1 | 3/2007 | Matthis et al. |
| 2007/0055242 A1 | 3/2007 | Bailly |
| 2007/0055244 A1 | 3/2007 | Jackson |
| 2007/0055247 A1 | 3/2007 | Jahng |
| 2007/0073289 A1 | 3/2007 | Kwak |
| 2007/0073290 A1 | 3/2007 | Boehm, Jr. |
| 2007/0073291 A1 | 3/2007 | Cordaro et al. |
| 2007/0073293 A1 | 3/2007 | Martz |
| 2007/0073405 A1 | 3/2007 | Chin et al. |
| 2007/0078460 A1 | 4/2007 | Frigg et al. |
| 2007/0078461 A1 | 4/2007 | Shluzas |
| 2007/0083199 A1 | 4/2007 | Baccelli |
| 2007/0088357 A1 | 4/2007 | Johnson et al. |
| 2007/0088359 A1 | 4/2007 | Woods et al. |
| 2007/0093813 A1 | 4/2007 | Callahan, II et al. |
| 2007/0093814 A1 | 4/2007 | Callahan, II et al. |
| 2007/0093815 A1 | 4/2007 | Callahan, II et al. |
| 2007/0093817 A1 | 4/2007 | Barrus et al. |
| 2007/0093818 A1 | 4/2007 | Biedermann et al. |
| 2007/0093819 A1 | 4/2007 | Albert |
| 2007/0093824 A1 | 4/2007 | Hestad et al. |
| 2007/0093826 A1 | 4/2007 | Hawkes et al. |
| 2007/0093827 A1 | 4/2007 | Warnick |
| 2007/0093828 A1 | 4/2007 | Abdou |
| 2007/0093831 A1 | 4/2007 | Abdelgany et al. |
| 2007/0093833 A1 | 4/2007 | Kuiper et al. |
| 2007/0100341 A1 | 5/2007 | Reglos et al. |
| 2007/0118117 A1 | 5/2007 | Altarac et al. |
| 2007/0118118 A1 | 5/2007 | Kwak et al. |
| 2007/0118119 A1 | 5/2007 | Hestad |
| 2007/0118122 A1 | 5/2007 | Butler et al. |
| 2007/0118123 A1 | 5/2007 | Strausbaugh et al. |
| 2007/0118124 A1 | 5/2007 | Biedermann et al. |
| 2007/0123862 A1 | 5/2007 | Warnick |
| 2007/0123864 A1 | 5/2007 | Walder et al. |
| 2007/0123865 A1 | 5/2007 | Schlapfer et al. |
| 2007/0123866 A1 | 5/2007 | Gerbec et al. |
| 2007/0123867 A1 | 5/2007 | Kirschman |
| 2007/0123870 A1 | 5/2007 | Jeon et al. |
| 2007/0123871 A1 | 5/2007 | Jahng |
| 2007/0129729 A1 | 6/2007 | Petit et al. |
| 2007/0135815 A1 | 6/2007 | Gerbec et al. |
| 2007/0161986 A1 | 7/2007 | Levy |
| 2007/0161991 A1 | 7/2007 | Altarac et al. |
| 2007/0161994 A1 | 7/2007 | Lowrey et al. |
| 2007/0161995 A1 | 7/2007 | Trautwein et al. |
| 2007/0161996 A1 | 7/2007 | Biedermann et al. |
| 2007/0161997 A1 | 7/2007 | Thramann et al. |
| 2007/0161999 A1 | 7/2007 | Biedermann et al. |
| 2007/0167948 A1 | 7/2007 | Abdou |
| 2007/0167949 A1 | 7/2007 | Altarac et al. |
| 2007/0173818 A1 | 7/2007 | Hestad et al. |
| 2007/0173819 A1 | 7/2007 | Sandlin |
| 2007/0173820 A1 | 7/2007 | Trieu |
| 2007/0173822 A1 | 7/2007 | Bruneau et al. |
| 2007/0173828 A1 | 7/2007 | Firkins et al. |
| 2007/0173832 A1 | 7/2007 | Tebbe et al. |
| 2007/0191839 A1 | 8/2007 | Justis et al. |
| 2007/0191841 A1 | 8/2007 | Justis et al. |
| 2007/0191846 A1 | 8/2007 | Bruneau et al. |
| 2007/0198014 A1 | 8/2007 | Graf et al. |
| 2007/0208344 A1 | 9/2007 | Young |
| 2007/0213720 A1 | 9/2007 | Gordon et al. |
| 2007/0225707 A1 | 9/2007 | Wisnewski et al. |
| 2007/0225708 A1 | 9/2007 | Biedermann et al. |
| 2007/0225710 A1 | 9/2007 | Jahng et al. |
| 2007/0225711 A1 | 9/2007 | Ensign |
| 2007/0233064 A1 | 10/2007 | Holt |
| 2007/0233073 A1 | 10/2007 | Wisnewski et al. |
| 2007/0233075 A1 | 10/2007 | Dawson |
| 2007/0233078 A1 | 10/2007 | Justis et al. |
| 2007/0233080 A1 | 10/2007 | Na et al. |
| 2007/0233085 A1* | 10/2007 | Biedermann et al. ............ 606/61 |
| 2007/0233086 A1 | 10/2007 | Harms et al. |
| 2007/0233087 A1 | 10/2007 | Schlapfer |
| 2007/0233092 A1 | 10/2007 | Falahee |
| 2007/0233094 A1 | 10/2007 | Colleran et al. |
| 2007/0233095 A1 | 10/2007 | Schlaepfer |
| 2007/0250061 A1 | 10/2007 | Chin et al. |
| 2007/0260243 A1 | 11/2007 | Biedermann |
| 2007/0270806 A1 | 11/2007 | Foley et al. |
| 2007/0270807 A1 | 11/2007 | Armstrong et al. |
| 2007/0270810 A1 | 11/2007 | Sanders |
| 2007/0270813 A1 | 11/2007 | Garamszegi |
| 2007/0270814 A1 | 11/2007 | Lim et al. |
| 2007/0270815 A1 | 11/2007 | Johnson et al. |
| 2007/0270821 A1 | 11/2007 | Trieu et al. |
| 2007/0270830 A1 | 11/2007 | Morrison |
| 2007/0270831 A1 | 11/2007 | Dewey et al. |
| 2007/0270832 A1 | 11/2007 | Moore |
| 2007/0270835 A1 | 11/2007 | Wisnewski |
| 2007/0270837 A1 | 11/2007 | Eckhardt et al. |
| 2007/0270838 A1 | 11/2007 | Bruneau et al. |
| 2007/0270839 A1 | 11/2007 | Jeon et al. |
| 2007/0270843 A1 | 11/2007 | Matthis et al. |
| 2007/0276380 A1 | 11/2007 | Jahng et al. |
| 2007/0288004 A1 | 12/2007 | Alvarez |
| 2007/0288008 A1 | 12/2007 | Park |
| 2007/0288009 A1 | 12/2007 | Logan |
| 2007/0288011 A1 | 12/2007 | Logan |
| 2007/0288012 A1 | 12/2007 | Colleran et al. |
| 2008/0009862 A1 | 1/2008 | Hoffman |
| 2008/0009864 A1 | 1/2008 | Forton et al. |
| 2008/0015578 A1 | 1/2008 | Erickson et al. |
| 2008/0015579 A1 | 1/2008 | Whipple |
| 2008/0015580 A1 | 1/2008 | Chao |
| 2008/0015584 A1 | 1/2008 | Richelsoph |
| 2008/0015586 A1 | 1/2008 | Krishna et al. |
| 2008/0021454 A1 | 1/2008 | Chao et al. |
| 2008/0021455 A1 | 1/2008 | Chao et al. |
| 2008/0021458 A1 | 1/2008 | Lim |
| 2008/0021459 A1 | 1/2008 | Lim |
| 2008/0021462 A1 | 1/2008 | Trieu |
| 2008/0021464 A1 | 1/2008 | Norin et al. |
| 2008/0021465 A1 | 1/2008 | Shadduck et al. |
| 2008/0021466 A1 | 1/2008 | Shadduck et al. |
| 2008/0021473 A1 | 1/2008 | Butler et al. |
| 2008/0027432 A1 | 1/2008 | Strauss et al. |
| 2008/0033435 A1 | 2/2008 | Studer et al. |
| 2008/0039838 A1 | 2/2008 | Landry et al. |
| 2008/0039843 A1 | 2/2008 | Abdou |
| 2008/0045951 A1 | 2/2008 | Fanger et al. |
| 2008/0045955 A1 | 2/2008 | Berrevoets et al. |
| 2008/0045957 A1 | 2/2008 | Landry et al. |
| 2008/0051780 A1 | 2/2008 | Vaidya et al. |
| 2008/0051787 A1 | 2/2008 | Remington et al. |
| 2008/0058811 A1 | 3/2008 | Alleyne et al. |
| 2008/0058812 A1 | 3/2008 | Zehnder |
| 2008/0065071 A1 | 3/2008 | Park |
| 2008/0065073 A1 | 3/2008 | Perriello et al. |
| 2008/0065075 A1 | 3/2008 | Dant |
| 2008/0065077 A1 | 3/2008 | Ferree |
| 2008/0065079 A1 | 3/2008 | Bruneau et al. |
| 2008/0071273 A1 | 3/2008 | Hawkes et al. |
| 2008/0071274 A1 | 3/2008 | Ensign |
| 2008/0071277 A1 | 3/2008 | Warnick |
| 2008/0077139 A1 | 3/2008 | Landry et al. |
| 2008/0086131 A1 | 4/2008 | Daly et al. |

(56) References Cited

U.S. PATENT DOCUMENTS

| | | |
|---|---|---|
| 2008/0086132 A1 | 4/2008 | Biedermann et al. |
| 2008/0091214 A1 | 4/2008 | Richelsoph |
| 2008/0097431 A1 | 4/2008 | Vessa |
| 2008/0097434 A1 | 4/2008 | Moumene et al. |
| 2008/0097441 A1 | 4/2008 | Hayes et al. |
| 2008/0097457 A1 | 4/2008 | Warnick |
| 2008/0108992 A1 | 5/2008 | Barry et al. |
| 2008/0119858 A1 | 5/2008 | Potash |
| 2008/0125777 A1 | 5/2008 | Veldman et al. |
| 2008/0125787 A1 | 5/2008 | Doubler et al. |
| 2008/0132952 A1 | 6/2008 | Malandain et al. |
| 2008/0140075 A1 | 6/2008 | Ensign et al. |
| 2008/0140076 A1 | 6/2008 | Jackson |
| 2008/0140133 A1 | 6/2008 | Allard et al. |
| 2008/0147122 A1 | 6/2008 | Jackson |
| 2008/0154307 A1 | 6/2008 | Colleran et al. |
| 2008/0161854 A1 | 7/2008 | Bae et al. |
| 2008/0161859 A1 | 7/2008 | Nilsson |
| 2008/0161863 A1 | 7/2008 | Arnold et al. |
| 2008/0167687 A1 | 7/2008 | Colleran et al. |
| 2008/0177316 A1 | 7/2008 | Bergeronk et al. |
| 2008/0177317 A1 | 7/2008 | Jackson |
| 2008/0177319 A1 | 7/2008 | Schwab |
| 2008/0177321 A1 | 7/2008 | Drewry et al. |
| 2008/0177322 A1 | 7/2008 | Davis et al. |
| 2008/0177327 A1 | 7/2008 | Malandain et al. |
| 2008/0183212 A1 | 7/2008 | Veldman et al. |
| 2008/0183213 A1 | 7/2008 | Veldman et al. |
| 2008/0183215 A1 | 7/2008 | Altarac et al. |
| 2008/0183216 A1 | 7/2008 | Jackson |
| 2008/0183219 A1 | 7/2008 | Jackson |
| 2008/0183223 A1 | 7/2008 | Jeon et al. |
| 2008/0195100 A1 | 8/2008 | Capote et al. |
| 2008/0195153 A1 | 8/2008 | Thompson |
| 2008/0215095 A1 | 9/2008 | Biedermann et al. |
| 2008/0221620 A1 | 9/2008 | Krause |
| 2008/0221692 A1 | 9/2008 | Zucherman et al. |
| 2008/0228227 A1 | 9/2008 | Brown et al. |
| 2008/0228229 A1 | 9/2008 | Walder et al. |
| 2008/0234691 A1 | 9/2008 | Schwab |
| 2008/0234734 A1 | 9/2008 | Wabler et al. |
| 2008/0234736 A1 | 9/2008 | Trieu et al. |
| 2008/0234737 A1 | 9/2008 | Bosehert |
| 2008/0234739 A1 | 9/2008 | Hudgins et al. |
| 2008/0234744 A1 | 9/2008 | Zylber et al. |
| 2008/0234746 A1 | 9/2008 | Jahng et al. |
| 2008/0243188 A1 | 10/2008 | Walder |
| 2008/0255617 A1 | 10/2008 | Cho et al. |
| 2008/0262546 A1 | 10/2008 | Calvosa et al. |
| 2008/0262548 A1 | 10/2008 | Lange et al. |
| 2008/0262552 A1 | 10/2008 | Kim |
| 2008/0262554 A1 | 10/2008 | Hayes et al. |
| 2008/0269804 A1 | 10/2008 | Holt |
| 2008/0275504 A1 | 11/2008 | Bonin et al. |
| 2008/0287994 A1 | 11/2008 | Perez-Cruet et al. |
| 2008/0300630 A1 | 12/2008 | Bohnema et al. |
| 2008/0300633 A1 | 12/2008 | Jackson |
| 2008/0306528 A1 | 12/2008 | Winslow et al. |
| 2008/0306533 A1 | 12/2008 | Winslow et al. |
| 2008/0306536 A1 | 12/2008 | Frig et al. |
| 2008/0306539 A1 | 12/2008 | Cain et al. |
| 2008/0306540 A1 | 12/2008 | Mitchell et al. |
| 2008/0306543 A1 | 12/2008 | Cain et al. |
| 2008/0306545 A1 | 12/2008 | Winslow |
| 2008/0312694 A1 | 12/2008 | Peterman et al. |
| 2009/0005817 A1 | 1/2009 | Friedrich et al. |
| 2009/0018583 A1 | 1/2009 | Song et al. |
| 2009/0024165 A1 | 1/2009 | Ferree |
| 2009/0024169 A1 | 1/2009 | Triplett et al. |
| 2009/0030464 A1 | 1/2009 | Hestad et al. |
| 2009/0030465 A1 | 1/2009 | Altarac et al. |
| 2009/0048631 A1 | 2/2009 | Bhatnagar et al. |
| 2009/0054932 A1 | 2/2009 | Butler et al. |
| 2009/0069849 A1 | 3/2009 | Oh et al. |
| 2009/0082815 A1 | 3/2009 | Zylber et al. |
| 2009/0088799 A1 | 4/2009 | Yeh |
| 2009/0088803 A1 | 4/2009 | Justis et al. |
| 2009/0093820 A1 | 4/2009 | Trieu et al. |
| 2009/0093843 A1 | 4/2009 | Lemoine et al. |
| 2009/0093845 A1 | 4/2009 | Hestad et al. |
| 2009/0093846 A1 | 4/2009 | Hestad et al. |
| 2009/0099606 A1 | 4/2009 | Hestad et al. |
| 2009/0099607 A1 | 4/2009 | Fallin et al. |
| 2009/0099608 A1 | 4/2009 | Szczesny |
| 2009/0105760 A1 | 4/2009 | Frey |
| 2009/0112265 A1 | 4/2009 | Hudgins et al. |
| 2009/0112266 A1 | 4/2009 | Weng et al. |
| 2009/0112267 A1 | 4/2009 | Atkinson et al. |
| 2009/0118767 A1 | 5/2009 | Hestad et al. |
| 2009/0125063 A1 | 5/2009 | Panjabi |
| 2009/0131981 A1 | 5/2009 | White |
| 2009/0138052 A1 | 5/2009 | Biedermann et al. |
| 2009/0149885 A1 | 6/2009 | Durwood et al. |
| 2009/0163953 A1 | 6/2009 | Biedermann et al. |
| 2009/0163954 A1 | 6/2009 | Kwak |
| 2009/0163955 A1 | 6/2009 | Moumene et al. |
| 2009/0171395 A1 | 7/2009 | Jeon et al. |
| 2009/0177232 A1 | 7/2009 | Kiester |
| 2009/0192548 A1 | 7/2009 | Jeon et al. |
| 2009/0198281 A1 | 8/2009 | Rice et al. |
| 2009/0228045 A1 | 9/2009 | Hayes et al. |
| 2009/0240286 A1 | 9/2009 | Friedrich et al. |
| 2009/0240287 A1 | 9/2009 | Cunliffe et al. |
| 2009/0248075 A1 | 10/2009 | Ogilvie et al. |
| 2009/0248077 A1 | 10/2009 | Johns |
| 2009/0248081 A1 | 10/2009 | LeHuec et al. |
| 2009/0248083 A1 | 10/2009 | Patterson et al. |
| 2009/0248088 A1 | 10/2009 | Biedermann |
| 2009/0254123 A1 | 10/2009 | Pafford et al. |
| 2009/0259257 A1 | 10/2009 | Prevost |
| 2009/0259258 A1 | 10/2009 | Perez-Cruet et al. |
| 2009/0270917 A1 | 10/2009 | Boehm |
| 2009/0270920 A1 | 10/2009 | Douget et al. |
| 2009/0270921 A1 | 10/2009 | Krause |
| 2009/0270922 A1 | 10/2009 | Biedermann et al. |
| 2009/0275981 A1 | 11/2009 | Abdelgany et al. |
| 2009/0275983 A1 | 11/2009 | Veldman et al. |
| 2009/0275986 A1 | 11/2009 | Prevost et al. |
| 2009/0281572 A1 | 11/2009 | White |
| 2009/0281573 A1 | 11/2009 | Biedermann et al. |
| 2009/0287250 A1 | 11/2009 | Molz, IV et al. |
| 2009/0287251 A1 | 11/2009 | Bae et al. |
| 2009/0287252 A1 | 11/2009 | Marik et al. |
| 2009/0299411 A1 | 12/2009 | Laskowitz et al. |
| 2009/0318968 A1 | 12/2009 | Duggal et al. |
| 2009/0326582 A1 | 12/2009 | Songer et al. |
| 2009/0326583 A1 | 12/2009 | Moumene et al. |
| 2010/0010544 A1 | 1/2010 | Fallin et al. |
| 2010/0030271 A1 | 2/2010 | Winslow et al. |
| 2010/0036420 A1 | 2/2010 | Kalfas et al. |
| 2010/0036422 A1 | 2/2010 | Flynn et al. |
| 2010/0036423 A1 | 2/2010 | Hayes et al. |
| 2010/0036424 A1 | 2/2010 | Fielding et al. |
| 2010/0036425 A1 | 2/2010 | Barrus et al. |
| 2010/0042155 A1 | 2/2010 | Biedermann et al. |
| 2010/0042156 A1 | 2/2010 | Harms et al. |
| 2010/0049254 A1 | 2/2010 | Biedermann et al. |
| 2010/0057125 A1 | 3/2010 | Viker |
| 2010/0057126 A1 | 3/2010 | Hestad |
| 2010/0063544 A1 | 3/2010 | Butler |
| 2010/0063545 A1 | 3/2010 | Richelsoph |
| 2010/0063547 A1 | 3/2010 | Morin et al. |
| 2010/0063551 A1 | 3/2010 | Richelsoph |
| 2010/0069964 A1 | 3/2010 | Lechmann |
| 2010/0087858 A1 | 4/2010 | Abdou |
| 2010/0087862 A1 | 4/2010 | Biedermann et al. |
| 2010/0087863 A1 | 4/2010 | Biedermann et al. |
| 2010/0087865 A1 | 4/2010 | Biedermann et al. |
| 2010/0088782 A1 | 4/2010 | Moumene et al. |
| 2010/0094348 A1 | 4/2010 | Biedermann et al. |
| 2010/0198261 A1 | 8/2010 | Trieu et al. |
| 2010/0198269 A1 | 8/2010 | Taylor et al. |
| 2010/0204736 A1 | 8/2010 | Biedermann et al. |
| 2010/0211104 A1 | 8/2010 | Moumene et al. |

(56) References Cited

U.S. PATENT DOCUMENTS

| | | |
|---|---|---|
| 2010/0222819 A1 | 9/2010 | Timm et al. |
| 2010/0228292 A1 | 9/2010 | Arnold et al. |
| 2010/0249843 A1 | 9/2010 | Wegrzyn, III |
| 2010/0256682 A1 | 10/2010 | Fallin et al. |
| 2010/0262187 A1 | 10/2010 | Marik et al. |
| 2010/0262190 A1 | 10/2010 | Ballard et al. |
| 2010/0274285 A1 | 10/2010 | Rouleau |
| 2010/0274287 A1 | 10/2010 | Rouleau et al. |
| 2010/0274288 A1 | 10/2010 | Prevost et al. |

FOREIGN PATENT DOCUMENTS

| | | |
|---|---|---|
| DE | 4239716 | 8/1994 |
| DE | 4425392 | 11/1995 |
| DE | 19509141 | 9/1996 |
| DE | 19509331 | 9/1996 |
| DE | 29806563 | 7/1998 |
| DE | 29810798 | 12/1999 |
| DE | 19951145 | 5/2001 |
| DE | 102007055745 | 7/2008 |
| EP | 0667127 | 8/1995 |
| EP | 0677277 | 10/1995 |
| EP | 0885598 | 12/1998 |
| EP | 1121902 | 8/2001 |
| EP | 1190678 | 3/2002 |
| EP | 1570795 | 2/2005 |
| EP | 1570795 | 9/2005 |
| EP | 1579816 | 9/2005 |
| EP | 1634537 | 3/2006 |
| FR | 2717370 | 9/1995 |
| FR | 2718946 | 10/1995 |
| FR | 2729291 | 7/1996 |
| FR | 2796545 | 1/2001 |
| FR | 2799949 | 4/2001 |
| FR | 2814936 | 4/2002 |
| FR | 2856578 | 6/2003 |
| FR | 2865373 | 1/2004 |
| FR | 2865375 | 1/2004 |
| FR | 2865377 | 1/2004 |
| FR | 2846223 | 4/2004 |
| FR | 2857850 | 4/2004 |
| FR | 2865378 | 10/2004 |
| GB | 1519139 | 7/1978 |
| GB | 2365345 | 2/2002 |
| GB | 2382304 | 5/2003 |
| JP | 2000325358 | 3/2000 |
| SU | 313538 | 10/1971 |
| WO | WO92/03100 | 3/1992 |
| WO | WO94/10927 | 5/1994 |
| WO | WO94/26191 | 11/1994 |
| WO | WO01/45576 | 6/2001 |
| WO | WO02/054966 | 7/2002 |
| WO | WO02/102259 | 12/2002 |
| WO | WO03/026523 | 4/2003 |
| WO | WO03/068088 | 8/2003 |
| WO | WO2004/041100 | 5/2004 |
| WO | WO2004/075778 | 9/2004 |
| WO | WO2004/089245 | 10/2004 |
| WO | WO2004/107997 | 12/2004 |
| WO | WO2005/000136 | 1/2005 |
| WO | WO2005/000137 | 1/2005 |
| WO | WO2005/020829 | 3/2005 |
| WO | WO2005/065374 | 7/2005 |
| WO | WO2005/065375 | 7/2005 |
| WO | WO2005/072632 | 8/2005 |
| WO | WO2005/082262 | 9/2005 |
| WO | WO2005/099400 | 10/2005 |
| WO | WO2005/104969 | 11/2005 |
| WO | WO2006/005198 | 1/2006 |
| WO | WO2006/012088 | 2/2006 |
| WO | WO2006/017616 | 2/2006 |
| WO | WO2006/020530 | 2/2006 |
| WO | WO2006/028537 | 3/2006 |
| WO | WO2006/086537 | 8/2006 |
| WO | WO2006/116662 | 11/2006 |
| WO | WO2006/119241 | 11/2006 |
| WO | WO2007/002409 | 1/2007 |
| WO | WO2007/118045 | 10/2007 |
| WO | WO2007/124222 | 11/2007 |
| WO | WO2007/124249 | 11/2007 |
| WO | WO2007/130835 | 11/2007 |
| WO | WO2007/130840 | 11/2007 |
| WO | WO2007/130941 | 11/2007 |
| WO | WO2008/045210 | 4/2008 |
| WO | WO2008/069420 | 6/2008 |
| WO | WO2008/088990 | 7/2008 |
| WO | WO2008/089075 | 7/2008 |
| WO | WO2008/140756 | 11/2008 |
| WO | WO2005/013839 | 2/2009 |
| WO | WO2009/036541 | 3/2009 |
| WO | WO2010/018316 | 2/2010 |
| WO | WO2010/018317 | 2/2010 |
| WO | WO 2010/019704 | 2/2010 |
| WO | WO 2010/019857 | 2/2010 |

OTHER PUBLICATIONS

Brochure of Spinal Concepts, an Abbott Laboratories Company, Pathfinder, Minimally Invasive Pedicle Fixation System, Publication Date: Nov. 2003.

Brochure of Spinal Concepts, InCompass, Thoracolumbar Fixation System, Publication Date: Oct. 2003.

Brochure of Spinal Concepts, Pathfinder, Minimally Invasive Pedicle Fixation System, Publication Date: May 2003.

Brochure of Spinal Concepts, Surgical Technique, InCompass, Thoracolumbar Fixation System, Publication Date: Oct. 2003.

Brochure of SpineLine, Current Concepts, Minimally Invasive Posterior Spinal Decompression and Fusion Procedures, Publication Date: Sep./Oct. 2003.

Brochure of Zimmer Spine, Inc., Dynesys® LIS Less Invasive Surgery, The Dynamic Stabilization System, Publication Date: 2005.

VLS System Variable Locking Screw Brochure, Interpore Cross International, 1999.

*EBI Omega 21* Brochure, EBI Spine Systems, pub. 1999.

*Claris Instrumentation* Brochure, G Med, pub. 1997.

*VLS System Variable Locking Screw* Brochure, Interpore Cross International, 1999.

*The Rod Plate System* Brochure, Stryker Howmedica Osteonics, pub. Oct. 1999.

*SDRS Surgical Dynamics Rod System* Brochure, Surgical Dynamics, pub. 1998-1999.

*Versalok Low Back Fixation System* Brochure, Wright Medical Technology, Inc., pub. 1997.

Brochure of Tyco/Healthcare/Surgical Dynamics on Spiral Radius 90D, Publication Date: Sep. 2001, pp. 1-8.

\* cited by examiner

DYNAMIC STABILIZATION CONNECTING MEMBER WITH ELASTIC CORE AND OUTER SLEEVE

CROSS REFERENCE TO RELATED APPLICATION

This application is a Continuation of U.S. application Ser. No. 11/894,001, filed Aug. 17, 2007, that claimed the benefit of U.S. Provisional Application No. 60/851,353, filed Oct. 12, 2006, the disclosures of both are incorporated by reference herein. U.S. application Ser. No. 11/894,001 also claimed the benefit of U.S. Provisional Application No. 60/905,472, filed Mar. 7, 2007, the disclosure of which is incorporated by reference herein. U.S. application Ser. No. 11/894,001 is also a continuation-in-part of U.S. patent application Ser. No. 11/522,503, filed Sep. 14, 2006 that claims the benefit of U.S. Provisional Application Nos. 60/722,300, filed Sep. 30, 2005; 60/725,445, filed Oct. 11, 2005; 60/728,912, filed Oct. 21, 2005; 60/736,112, filed Nov. 10, 2005, and 60/832,644, filed Jul. 21, 2006; the disclosures all of which are incorporated by reference herein.

BACKGROUND OF THE INVENTION

The present invention is directed to dynamic fixation assemblies for use in bone surgery, particularly spinal surgery, and in particular to longitudinal connecting members and cooperating bone anchors or fasteners for such assemblies, the connecting members being attached to at least two bone fasteners.

Historically, it has been common to fuse adjacent vertebrae that are placed in fixed relation by the installation therealong of bone screws or other bone anchors and cooperating longitudinal connecting members or other elongate members. Fusion results in the permanent immobilization of one or more of the intervertebral joints. Because the anchoring of bone screws, hooks and other types of anchors directly to a vertebra can result in significant forces being placed on the vertebra, and such forces may ultimately result in the loosening of the bone screw or other anchor from the vertebra, fusion allows for the growth and development of a bone counterpart to the longitudinal connecting member that can maintain the spine in the desired position even if the implants ultimately fail or are removed. Because fusion has been a desired component of spinal stabilization procedures, longitudinal connecting members have been designed that are of a material, size and shape to largely resist flexure, extension, torsion, distraction and compression, and thus substantially immobilize the portion of the spine that is to be fused. Thus, longitudinal connecting members are typically uniform along an entire length thereof, and usually made from a single or integral piece of material having a uniform diameter or width of a size to provide substantially rigid support in all planes.

Fusion, however, has some undesirable side effects. One apparent side effect is the immobilization of a portion of the spine. Furthermore, although fusion may result in a strengthened portion of the spine, it also has been linked to more rapid degeneration and even hyper-mobility and collapse of spinal motion segments that are adjacent to the portion of the spine being fused, reducing or eliminating the ability of such spinal joints to move in a more normal relation to one another. In certain instances, fusion has also failed to provide pain relief.

An alternative to fusion and the use of more rigid longitudinal connecting members or other rigid structure has been a "soft" or "dynamic" stabilization approach in which a flexible loop-, S-, C- or U-shaped member or a coil-like and/or a spring-like member is utilized as an elastic longitudinal connecting member fixed between a pair of pedicle screws in an attempt to create, as much as possible, a normal loading pattern between the vertebrae in flexion, extension, distraction, compression, side bending and torsion. Problems may arise with such devices, however, including tissue scarring, lack of adequate spinal support and lack of fatigue strength or endurance limit. Fatigue strength has been defined as the repeated loading and unloading of a specific stress on a material structure until it fails. Fatigue strength can be tensile or distraction, compression, shear, torsion, bending, or a combination of these.

Another type of soft or dynamic system known in the art includes bone anchors connected by flexible cords or strands, typically made from a synthetic polymer material. Such a cord or strand may be threaded through cannulated spacers that are disposed between adjacent bone anchors when such a cord or strand is implanted, tensioned and attached to the bone anchors. The spacers typically span the distance between bone anchors, providing limits on the bending movement of the cord or strand and thus strengthening and supporting the overall system. Such cord or strand-type systems require specialized fixed or non-polyaxial bone anchors as well as tooling for tensioning and holding the cord or strand in the bone anchors. Although flexible, the cords or strands utilized in such systems do not allow for elastic distraction or stretchability of the system once implanted because the cord or strand must be stretched or pulled to maximum tension during installation in order to provide a stable, supportive system. In addition, because the bone anchors are fixed and not polyaxial they are more difficult to use.

The complex dynamic conditions associated with spinal movement therefore provide quite a challenge for the design of more flexible elongate longitudinal connecting members that exhibit an adequate fatigue strength to provide stabilization and protected motion of the spine, without fusion, and allow for some natural movement of the portion of the spine being reinforced and supported by the elongate flexible connecting member.

SUMMARY OF THE INVENTION

Longitudinal connecting member assemblies according to the invention for use between at least two bone anchors provide dynamic, protected motion of the spine. A longitudinal connecting member assembly according to the invention has an inner elastic core. An outer sleeve or spacer surrounds the core, the sleeve extending between a pair of adjacent bone anchors. The elastic core and outer sleeve cooperate dynamically, both features having some elasticity and flexibility, with the outer sleeve primarily protecting and limiting flexing or bending movement of the inner core. The inner core can be of varying degrees of firmness and of any cross-sectional shape. The outer sleeve may include a grooved portion facilitating compression of the sleeve against the pair of bone anchors upon installation therebetween. The outer sleeve also can be of varying degrees of firmness and of any cross-sectional shape. As compared to dynamic systems that include flexible cords and spacers, embodiments according to the present invention advantageously allow for elastic distraction or stretchability of the connecting member assembly and the use of closed and open-ended bone anchors, as well as fixed and polyaxial bone anchors.

OBJECTS AND ADVANTAGES OF THE INVENTION

Therefore, it is an object of the present invention to overcome one or more of the problems with bone attachment assemblies described above. An object of the invention is to provide dynamic medical implant stabilization assemblies having longitudinal connecting members that include an elastic inner core that allows for bending, torsion, compression and distraction of the assembly. Another object of the invention is to provide such an assembly wherein the elastic portion is insertable into a protective outer sleeve. A further object of the invention is to provide such an assembly wherein the outer sleeve may be compressed upon installation. A further object of the invention is to provide dynamic medical implant longitudinal connecting members that may be utilized with a variety of bone screws, hooks and other bone anchors, including fixed and polyaxial implants. Additionally, it is an object of the invention to provide a lightweight, reduced volume, low profile assembly including at least two bone anchors and a longitudinal connecting member therebetween. Furthermore, it is an object of the invention to provide apparatus and methods that are easy to use and especially adapted for the intended use thereof and wherein the apparatus are comparatively inexpensive to make and suitable for use.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. It is also noted that any reference to the words side, top, bottom, up and down, front and back and the like, in this application refers to the alignment shown in the various drawings, as well as the normal connotations applied to such devices, and is not intended to restrict positioning of the connecting member assemblies of the application and cooperating bone anchors in actual use.

With reference to FIGS. 1-5, the reference numeral 1 generally designates a non-fusion dynamic stabilization longitudinal connecting member assembly according to the present invention. The connecting member assembly 1 includes an inner core 8 and an outer sleeve or spacer 10. The inner core 8 is elongate having a central longitudinal axis A and also including a first end portion or section 16, an opposite second end portion or section 18 and a mid-portion or section 20 with all of the portions 16, 18 and 20 extending along the axis A. It is foreseen that the inner core 8 may further include a small central lumen or through bore extending along the axis A for receiving a guide wire in a percutaneous or minimally invasive surgical procedure. The inner core 8 is receivable in the outer sleeve 10 with the outer sleeve 10 ultimately in position at the mid-portion or section 20.

Figures 4, 5:
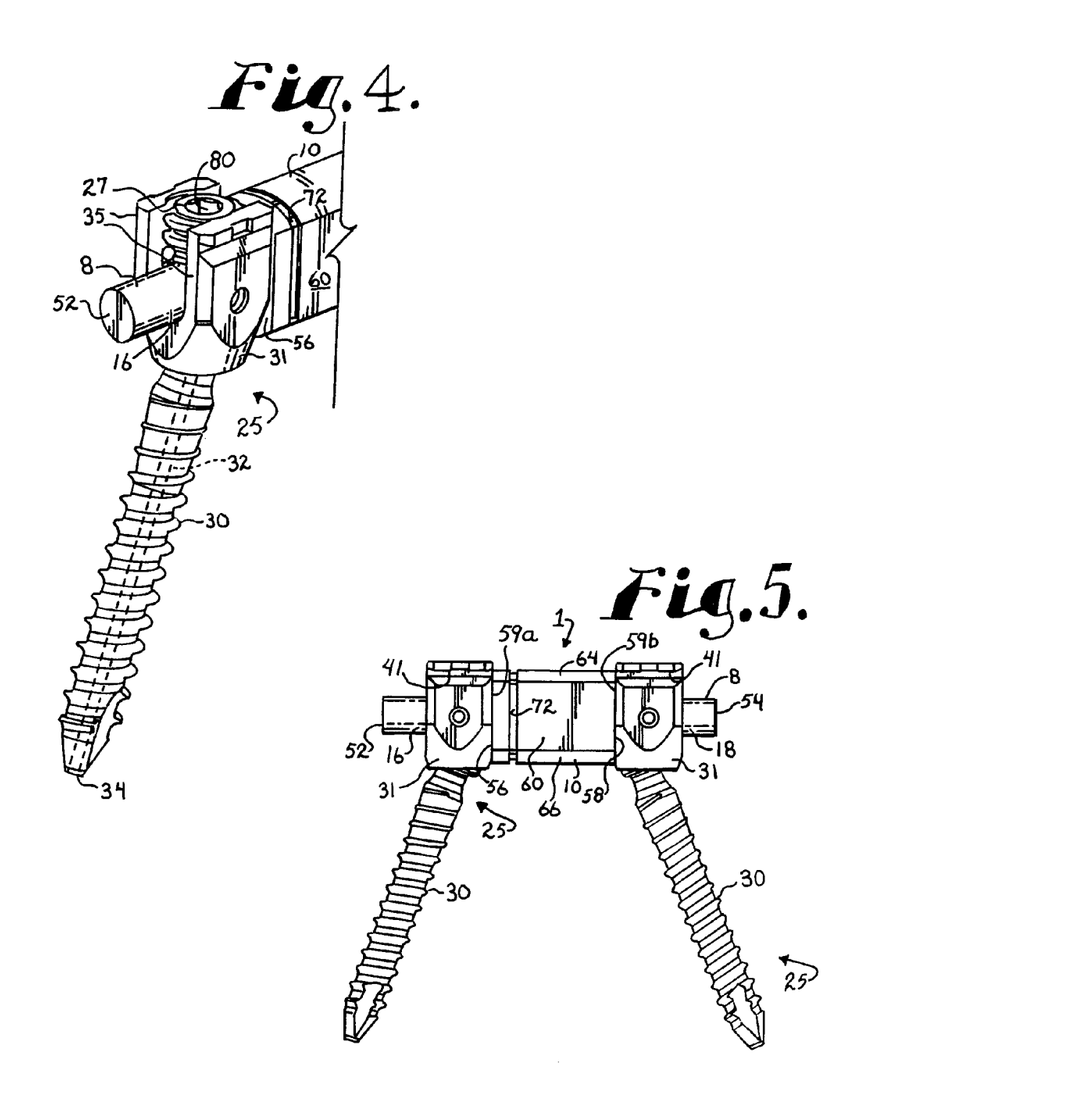
FIG. 4 is an enlarged and partial perspective view of the connecting member assembly of FIG. 1 shown with a polyaxial bone screw and cooperating closure member.
FIG. 5 is a front elevational view of the connecting member assembly as illustrated in FIG. 2 and further shown with a pair of polyaxial bone screws.

The dynamic connecting member assembly 1 cooperates with at least a pair of bone anchors, such as the polyaxial bone screws, generally 25 and cooperating closure structures 27 shown in FIGS. 4-5, the assembly 1 being captured and fixed in place at the end portions 16 and 18 by cooperation between the bone screws 25 and the closure structures 27. The sleeve 10 is sized and shaped for frictional engagement with each of a pair of bone screws 25 or other bone anchors, cooperating with the inner core 8 to support vertebrae adjacent thereto.

Because the end portions 16 and 18 are substantially solid, firm and cylindrical, the connecting member assembly 1 may be used with a wide variety of bone anchors already available for cooperation with more rigid rods including fixed, monoaxial bone screws, hinged bone screws, polyaxial bone screws, and bone hooks and the like, with or without upper and/or lower compression inserts or members, that may in turn cooperate with a variety of closure structures having threads, flanges, or other structure for fixing the closure structure to the bone anchor, and may include other features, for example, break-off tops and inner set screws. The bone anchors, closure structures and the connecting member assembly 1 are then operably incorporated in an overall spinal implant system for correcting degenerative conditions, deformities, injuries, or defects to the spinal column of a patient.

The polyaxial bone screws 25 illustrated in FIGS. 4 and 5 each include a shank 30 for insertion into a vertebra (not shown), the shank 30 being pivotally attached to an open receiver or head 31. The shank 30 includes a threaded outer surface and may further include a central cannula or through-bore 32 disposed along an axis of rotation of the shank, the through-bore 32 extending between a top surface and a bottom surface 34 of the shank 30. The bore 32 provides a passage through the shank interior for a length of wire or pin inserted into the vertebra prior to the insertion of the shank 30, the wire or pin providing a guide for insertion of the shank 30 into the vertebra.

The receiver 31 has a pair of spaced and generally parallel arms 35 that form an open generally U-shaped or squared shaped channel therebetween that is open at distal or front and back ends of the arms 35. The arms 35 each include radially inward or interior surfaces that have a discontinuous guide and advancement structure mateable with cooperating structure on the closure structure 27. The guide and advancement structure may be a partial helically wound flangeform configured to mate under rotation with a similar structure on the closure structure 27 or a buttress thread, a square thread, a reverse angle thread or other thread like or non-thread like helically wound advancement structures for operably guiding under rotation and advancing the closure structure 27 downward between the receiver arms 35 and having such a nature as to resist splaying of the arms 35 when the closure 27 is advanced between the arms 35.

Each of the arms 35 also includes a V-shaped or undercut tool engagement groove 41 formed on a substantially planar outer surface thereof which may be used for holding the receiver 31 with a holding tool (not shown) having projections that are received within the grooves 41 during implantation of the shank 30 into the vertebra (not shown). The grooves 41 may also cooperate with a holding tool during bone screw assembly and during subsequent installation of the connecting member assembly 1 and the closure structure 27. It is foreseen that tool receiving grooves or apertures may be configured in a variety of shapes and sizes and be disposed at other locations on the receiver arms 35 for use with open and minimally invasive surgical techniques (MIS).

The shank 30 and the receiver 31 may be attached in a variety of ways. For example, a spline capture connection as described in U.S. Pat. No. 6,716,214, and incorporated by reference herein, may be used wherein the bone screw shank includes a capture structure mateable with a retaining structure disposed within the receiver. The retaining structure includes a partially spherical surface that is slidingly mateable with a cooperating inner surface of the receiver 31, allowing for a wide range of pivotal movement between the shank 30 and the receiver 31. It is also foreseen that the shank 30 and the retaining structure can be crimped or pinned together. Polyaxial bone screws with other types of capture and retaining connections may also be used according to the invention, including but not limited to camming and wedging connections, spherical connections, threaded connections, frictional connections utilizing frusto-conical or polyhedral capture structures, integral top or downloadable shanks, top and bottom loaded retainer rings that are integral, slotted or more than one piece, and the like. For example, with reference to FIGS. 11 and 12, a threaded connection is shown and is described in greater detail below. Also, as indicated above, polyaxial and other bone screws for use with connecting members of the invention may have bone screw shanks that attach directly to the connecting member or may include one or more pressure or compression members or inserts that cooperate with the bone screw shank, receiver and closure structure to secure the connecting member assembly to the bone screw and/or fix the bone screw shank at a desired angle with respect to the bone screw receiver that holds the longitudinal connecting member assembly. For example, with reference to FIGS. 11 and 12, both upper and lower pressure inserts are shown. Furthermore, although the closure structure 27 of the present invention is illustrated with the polyaxial bone screw 25 having an open receiver or head 31, it foreseen that a variety of closure structure may be used in conjunction with any type of medical implant having an open or closed head, including monoaxial bone screws, hinged bone screws, hooks and the like used in spinal surgery. It is foreseen that the front and back planar surfaces of the fixed screw heads can be convergent or divergent.

To provide a biologically active interface with the bone, the threaded shank 30 may be coated, perforated, made porous or otherwise treated. The treatment may include, but is not limited to a plasma spray coating or other type of coating of a metal or, for example, a calcium phosphate; or a roughening, perforation or indentation in the shank surface, such as by sputtering, sand blasting or acid etching, that allows for bony ingrowth or ongrowth. Certain metal coatings act as a scaffold for bone ingrowth. Bio-ceramic calcium phosphate coatings include, but are not limited to: alpha-tri-calcium phosphate and beta-tri-calcium phosphate $(Ca_3(PO_4)_2$, tetra-calcium phosphate $(Ca_4P_2O_9)$, amorphous calcium phosphate and hydroxyapatite $(Ca_n(PO_4)_6(OH)_2)$. Coating with hydroxyapatite, for example, is desirable as hydroxyapatite is chemically similar to bone with respect to mineral content and has been identified as being bioactive and thus not only supportive of bone ingrowth, but actively taking part in bone bonding.

Figures 11, 12:
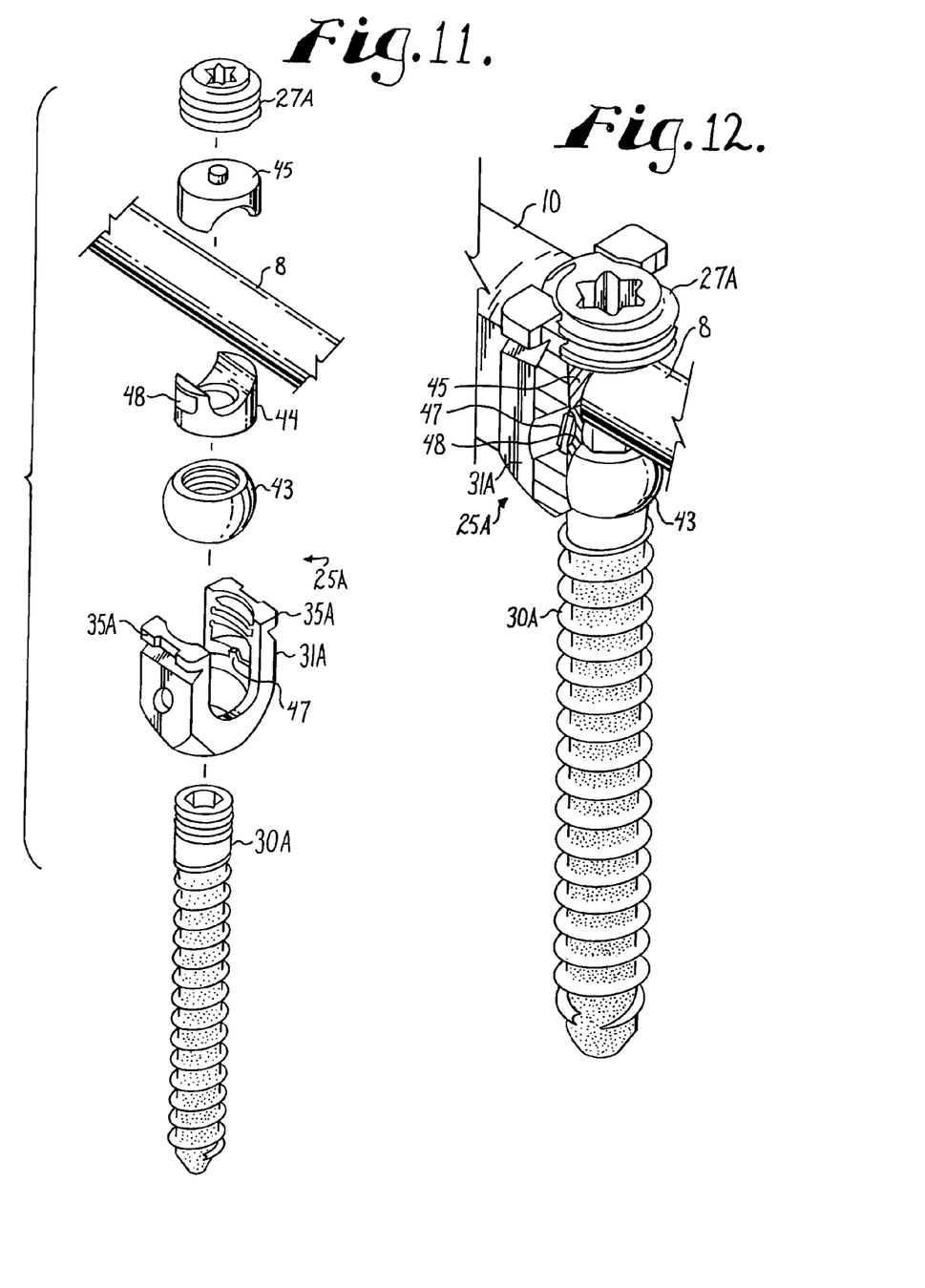
FIG. 11 is an enlarged exploded partial perspective view of the core of FIG. 1 shown with an alternative polyaxial bone screw.
FIG. 12 is an enlarged and partial perspective view of the assembly of FIG. 1 shown assembled with the polyaxial bone screw of FIG. 11 and with portions broken away to show the detail thereof.

With reference to FIGS. 11 and 12, the longitudinal connecting member 1 is shown cooperating with an alternative polyaxial screw assembly, generally 25A and a closure structure 27A. The polyaxial bone screw 25A includes a shank 30A for insertion into a vertebra (not shown), the shank 30 being pivotally attached to an open receiver or head 31A. The shank 30A includes a threaded outer surface and may further include a central cannula or through-bore disposed along an axis of rotation of the shank, the through-bore being similar to the bore 32 previously described herein with respect to the shank 30. The receiver 31A has a pair of spaced and generally parallel arms 35A that form an open generally U-shaped channel therebetween that is open at distal ends or front and back sides of the arms 35A. The arms 35A each include radially inward or interior surfaces that have a discontinuous guide and advancement structure mateable with cooperating structure on the closure structure 27A. The shank 30A and the receiver 31A are pivotally attached utilizing a retaining structure or ring 43 that threadably mates with the shank 30A. Furthermore a lower compression insert 44 and an upper compression insert 45 are received in the receiver 31A and closely receive, support and hold the core 8 of the longitudinal connecting member assembly 1. The shank 30A, the retaining structure 43 and the lower and upper compression inserts 44 and 45, respectively, are described in greater detail in U.S. patent application Ser. No. 11/522,503, filed Sep. 14, 2006, the disclosure of which is incorporated by reference herein. The receiver 31A further includes compression insert alignment and retention structures in the form of a pair of spring tabs 47. The tabs 47 cooperate with grooved or flat surfaces 48 on the lower compression insert 44 to hold the insert 44 in proper alignment with respect to the cylindrical core 8. The spring tabs 47 and cooperating insert surfaces 48 are described in greater detail in U.S. Provisional Patent Application Ser. No. 60/905,472 filed Mar. 7, 2007, the disclosure of which is incorporated by reference herein.

The longitudinal connecting member assembly 1 illustrated in FIGS. 1-5 and 11-12 is elongate, with the inner core 8 being an elastic substantially solid, somewhat firm, smooth and uniform cylinder or rod having an outer cylindrical surface 50 and a circular cross-section. The core 8 is made from natural or synthetic elastomers, including, but not limited to polyisoprene (natural rubber), and synthetic polymers, copolymers, and thermoplastic elastomers, for example, polyurethane elastomers, including polycarbonate-urethanes. It is foreseen that one portion or segment of the connecting member could be made from metal, etc. and affixed to the elastomer portion. The illustrated sleeve 10 is also made from a plastic, such as a thermoplastic elastomer, for example, polycarbonate-urethane having a greater stiffness than the elastomer of the core 8. In order to have low or no wear debris, the sleeve 10 inner surfaces and/or cooperating core 8 outer surfaces may be coated with an ultra thin, ultra hard, ultra slick and ultra smooth coating, such as may be obtained from ion bonding techniques and/or other gas or chemical treatments.

The illustrated core 8 has an end 52 and an opposite end 54, with the solid end portion 16 terminating at the end 52 and the solid end portion 18 terminating at the end 54. The portions 16 and 18 are each sized and shaped to be received in the U-shaped channel of a bone screw 25 with the mid-portion 20 sized and shaped to extend between cooperating bone screws 25. The sleeve 10 advantageously cooperates with the mid-portion 20, providing limitation and protection of movement of the core 8 at the portion 20. Thus, with reference to FIG. 5, the sleeve 10 is sized and shaped for substantially even and precise alignment and substantial frictional contact between flat end surfaces 56 and 58 of the sleeve 10 and cooperating flat planar side surfaces 59a and 59b of the receivers 31. The sleeve 10 can be cut to any length needed.

Furthermore, also with reference to FIGS. 5 and 12, and as will be discussed in greater detail below, when the sleeve 10 is implanted, and the closure structures 27 or 27A are tightened in place in the receivers 31 or 31A, the tools utilized to implant the assembly 1 and/or the bone screws 25 or 25A are manipulated to direct the pair of adjacent receivers 31 or 31A toward one another so as to axially compress the elastic sleeve 10 (now situated substantially coaxial with the core 8 axis A) between facing side surfaces, for example, surfaces 59a and 59b of the adjacent receivers 31 shown in FIG. 5. Such compression due to frictional engagement and compression of the sleeve 10 between the bone screw side surfaces 59a and 59b during installation results in some tension and distraction of the mid-portion 20 of the core 8 when the implantation tools are removed from the bone screws 25, as the sleeve end surfaces 56 and 58 then press against the facing bone screw surfaces 59a and 59b, but the core 8 is otherwise fixed with respect to each of the bone screws 25 within respective receiver 31 channels. Such dynamic tension/compression relationship between the sleeve 10 and the elastic core 8 provides further strength and stability to the overall assembly and also allows for the entire connecting member assembly 1 to elongate, if needed, in response to spinal movement. The increased stability and strength of the assembly advantageously allows for use of a smaller, more compact, reduced volume, lower profile longitudinal connecting member assembly 1 and cooperating bone anchors than, for example, flexible cord and spacer type longitudinal connecting member assemblies.

Figures 2, 3:
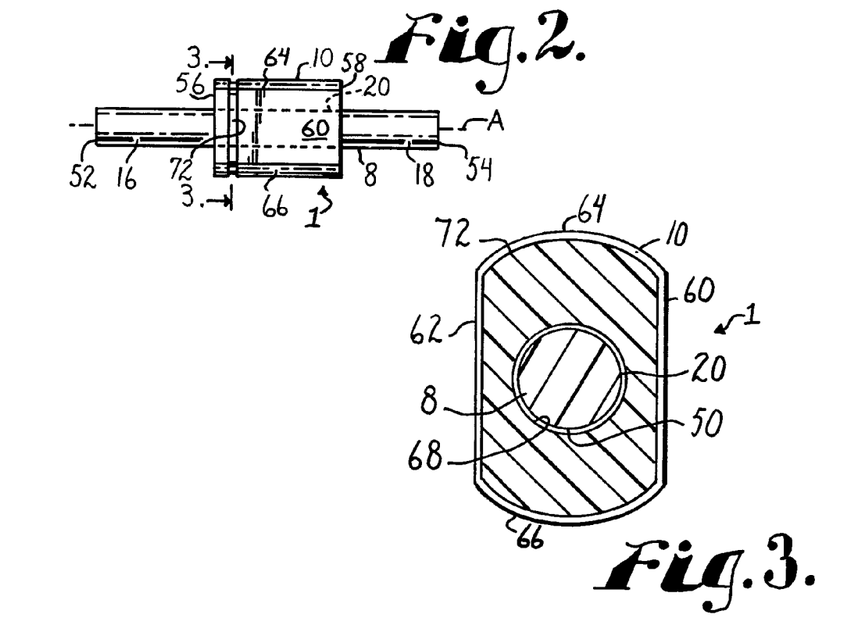
FIG. 2 is a front elevational view of the assembly of FIG. 1 shown assembled.
FIG. 3 is an enlarged cross-sectional view taken along the line 3-3 of FIG. 2.

The sleeve 10 further includes a pair of substantially flat parallel and opposite lateral surfaces 60 and 62 and a pair of curved opposite posterior/anterior surfaces 64 and 66. Each of the surfaces 60, 62, 64 and 66 extend between the flat end surfaces 56 and 58. The illustrated surfaces 64 and 66 have substantially the same radius originating along a central axis of the sleeve 10, such axis being coaxial with the axis A when the core 8 is inserted in the sleeve 10. As illustrated in FIG. 3, the geometry of the sleeve 10 allows for a narrower width between the parallel surfaces 60 and 62 than a distance or diameter between the curved surfaces 64 and 66. Such geometry provides adequate stiffness or support for the flexible core 8 in flexing due to the distance between the posterior/anterior curved surfaces 64 and 66, while the more narrow width or distance between the flat surfaces 60 and 62 allows for placement of the sleeve 10 between adjacent vertebrae without engagement with such vertebrae. Stated in another way, a cylindrical sleeve having a diameter large enough to produce a desired limit of bending or flexing movement of the core 8 would most likely have a diameter large enough to result in interference of the sleeve cylindrical surface with portions of adjacent vertebrae. The flat surfaces 60 and 62 allow for adequate clearance but do not detract from an overall strength of the sleeve 10.

Extending along the substantially central axis of the sleeve 10 (that corresponds to the axis A when the core 8 is disposed in the sleeve 10) is an internal substantially cylindrical and smooth surface 68. The surface 68 defines a bore 70 with a circular cross section, the bore 70 extending through the sleeve 10 and sized and shaped to receive the core 8. The internal surface 68 is of a slightly greater diameter than an outer diameter of the cylindrical surface 50 of the core 8, allowing for axially directed sliding movement of the sleeve 10 with respect to the core 8 during installation of the core 8 into the sleeve 10 and also when both the core 8 and the sleeve 10 are implanted with the sleeve 10 located between adjacent bone screws 25.

In the illustrated embodiment, the sleeve 10 further includes a compression groove 72. Sleeves 10 according to the invention may include one, none or any desired number of grooves 72. The groove 72 extends substantially uniformly about the sleeve 10 as illustrated in FIG. 3, being formed in the external surfaces 60, 62, 64 and 66 of the sleeve 10. The groove or grooves 72 may be added as desired to advantageously increase a longitudinal compressibility of the sleeve 10 during installation between a pair of bone screws 25 as previously described herein.

It is foreseen that the core 8 may be sized and shaped and made from such materials so as to provide for a relatively more rigid assembly 1 or a relatively more flexible assembly 1 with respect to flex or bendability along the assembly 1. Also, since the distance between the bone screw receivers or heads 31 can vary, the core 8 may need to be more or less stiff. Hybrid constructs are possible consisting of more rigid metals or PEEK material connected to less rigid elastic cores.

With reference to FIG. 4, the closure structure 27 can be any of a variety of different types of closure structures for use in conjunction with the present invention with suitable mating structure on the interior surface of the upstanding arms 35 of the receiver 31. The illustrated closure structure 27 is rotatable between the spaced arms 35, but could be a slide-in closure structure. The illustrated closure structure 27 is substantially cylindrical and includes an outer helically wound guide and advancement structure in the form of a flange form that may take a variety of forms, including those described in Applicant's U.S. Pat. No. 6,726,689, which is incorporated herein by reference. It is also foreseen that according to the invention the closure structure guide and advancement structure could alternatively be a buttress thread, a square thread, a reverse angle thread or other thread like or non-thread like helically wound advancement structure for operably guiding under rotation and advancing the closure structure 27 downward between the arms 35 and having such a nature as to resist splaying of the arms 35 when the closure structure 27 is advanced into the U-shaped channel formed by the arms 35. The illustrated closure 27 has an internal drive in the form of an aperture 80 utilized for assembly and removal of the closure 27. It is foreseen that the closure structure 27 may alternatively include an external drive, such as a break-off head designed to allow such a head to break from a base of the closure at a preselected torque, for example, 70 to 140 inch pounds. Such a closure structure would also include a base having an internal drive to be used for closure removal.

In use, at least two bone screws 25 or 25A are implanted into vertebrae for use with the longitudinal connecting member assembly 1. Each vertebra may be pre-drilled to minimize stressing the bone. Furthermore, when a cannulated bone screw shank is utilized, each vertebra will have a guide wire or pin (not shown) inserted therein that is shaped for the bone screw cannula, such as the cannula 32 of the bone screw shank 30, and provides a guide for the placement and angle of the shank 30 or 30A with respect to the cooperating vertebra. A further tap hole may be made and the shank 30 or 30A is then driven into the vertebra by rotation of a driving tool (not shown) that engages a driving feature (not shown) of the shank 30 or 30A. It is foreseen that the screws 25 or 25A and the longitudinal connecting member 1 can be inserted in a percutaneous or minimally invasive surgical manner.

Figure 1:
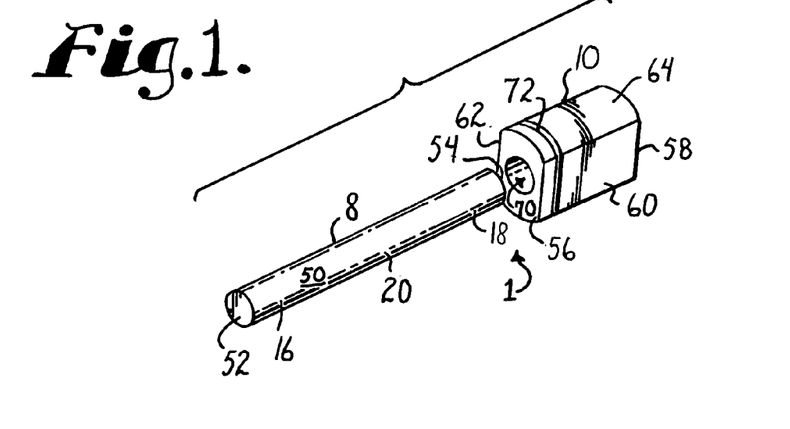
FIG. 1 is an exploded perspective view of a dynamic fixation connecting member assembly according to the invention including an elastic inner core and an outer sleeve.

With particular reference to FIGS. 1 and 2, the longitudinal connecting member assembly 1 is assembled by inserting the core 8 into the bore 70 defined by the inner cylindrical surface 68 of the outer sleeve 10. In the illustrated embodiment, the end 54 of the core 8 is placed into the bore 70 at the surface 56 and the sleeve 10 is moved toward the end portion 16 until the sleeve 10 is positioned between the end portions 16 and 18 and is disposed about the mid-portion 20. It is noted that in the illustrated embodiment, the core 8 and the sleeve 10 may also be assembled in other ways, for example, by inserting the end 52 of the core 8 into the bore 70 at either the end surface 56 or the end surface 58.

With reference to FIGS. 4 and 5, the connecting member assembly 1 is eventually positioned in an open or percutaneous manner in cooperation with the at least two bone screws 25 with the sleeve 10 disposed between the two bone screws 25 and the end portions 16 and 18 each within the U-shaped channels formed by the arms 35 of the two bone screws 25. The sleeve 10 is positioned between the bone screws 25 with the flat surfaces 60 and 62 substantially aligned with the arms 35 of the receivers 31 and the curved surfaces 64 and 66 placed in posterior and anterior positions with respect to the patient's body. Because the sleeve 10 is substantially symmetrical, either the surface 64 or the surface 66 may be placed either anteriorly or posteriorly. In the illustrated embodiment, the surface 64 is in a posterior position facing away from the overall bone screw and connecting member assembly while the surface 66 faces anteriorly generally directed toward the bone screw shanks 30.

A closure structure 27 or 27A is then inserted into and advanced between the arms 35 or 35A of each of the bone screws 25 or 25A. The closure structure 27 or 27A is rotated, using a tool engaged with the inner drive 80 until a selected pressure is reached at which point the core 8 is urged toward, but not completely seated in the bone screw 27 or 27A channels. For example, about 80 to about 120 inch pounds pressure may be required for fixing the bone screw shank 30 or 30A relative to the respective receiver 31 or 31A.

In the embodiment illustrated in FIGS. 4-5, downward movement of the closure structure 27 into the channel 37 presses a respective end portion 16 or 18 downward into engagement with a top or other upper portion of the respective bone screw shank 30, pressing a structure that is fixed or integral with the shank 30 into engagement with an inner surface of the respective receiver 31, thus setting an angle of articulation of the respective shank 30 with respect to the respective receiver 31, clamping the shank 30 into a fixed position with respect to the receiver 31. The receiver 31 and shank 30 may thus be secured at any of a plurality of angles, articulations or rotational alignments relative to one another and within a selected range of angles both from side to side and from front to rear, to enable flexible or articulated engagement of the receiver 31 with the shank 30 until both are locked or fixed relative to each other.

Alternatively, with reference to FIGS. 11 and 12, upper and/or lower compression inserts may be provided to aid in holding the core 8 within the receiver 31A and fixing the shank 30A with respect to the receiver 31A. Furthermore, the assembly 1 may cooperate with an open receiver that is integral or fixed in position with respect to a bone screw shank or bone hook, or with a receiver having limited angular movement with respect to the shank, such as a hinged connection, also with or without other compression members or inserts for fixing the assembly 1, the receiver and/or the bone anchor in a desired position or orientation with respect to the cooperating vertebrae.

As indicated previously herein, with reference to FIG. 5, as the closure structures 27 are rotated and then tightened against the end portions 16 and 18 within a pair of spaced bone screws 25, such bone screws 25 may be pressed toward one another, the facing surfaces 59a and 59b being moved toward one another, thereby frictionally engaging and then compressing the sleeve 10 between the surfaces 59a and 59b. When the insertion and tightening tools are removed, the sleeve 10, pressing against facing surfaces 59a and 59b of the cooperating bone screw receivers 31, stretches the elastic mid-portion 20 of the core 8. The assembly 1 is thus substantially dynamically loaded and oriented relative to the cooperating vertebrae to provide relief (e.g., shock absorption) and protected movement with respect to flexion, extension, distraction and compressive forces placed on the assembly 1 and the two connected bone screws 25. The elasticity of the core 8 may also allow the core 8 to twist or turn along its axis providing relief for torsional stresses and torsional spring back. The sleeve 10 limits such torsional movement as well as bending movement of the core 8, providing spinal support. Furthermore, because the sleeve 10 is compressed during installation, the sleeve advantageously allows for some protected extension or distraction of both the core 8 and the sleeve 10, which is not possible with a tight, taut unyielding core, as well as compression of the assembly 1 in cooperation with the core 8.

If removal of the assembly 1 from any of the bone screws 25 or 25A is necessary, or if it is desired to release the assembly 1 at a particular location, disassembly is accomplished by using the driving tool (not shown) inserted in the aperture 80 to rotate and remove the closure structure 27 or 27A from the receiver 31 or 31A. Disassembly is then accomplished in reverse order to the procedure described previously herein for assembly.

Eventually, if the spine requires more rigid support, the connecting member assembly 1 according to the invention may be removed and replaced with another longitudinal connecting member, such as a solid metal or PEEK rod, having the same diameter as the inner core 8 end portions 16 and 18, utilizing the same or same sized receivers 31 or 31A and closure structures 27 or 27A. Alternatively, if less support is eventually required, a less rigid, more flexible assembly, for example, an assembly 1 made with a more flexible core 8, but with end portions having the same diameter as the inner core 8 end portions 16 and 18, may replace the assembly 1, also utilizing the same bone screws 25. Also, with reference to FIGS. 6-10 and described more fully below, the core 8 and cooperating sleeve 10 may be replaced with a more or less flexible core 8A, 8B, 8C, 8D or 8E having a different cross-sectional shape that is receivable in a sleeve having a similarly shaped through bore, as well as mating upper compression inserts.

It is foreseen that longitudinal connecting member assemblies according to the invention may be of a variety of lengths for cooperation with a plurality of bone screws 25. With reference to FIGS. 6-10, the assemblies may also have inner cores of a variety of shapes and sizes.

Figure 6:
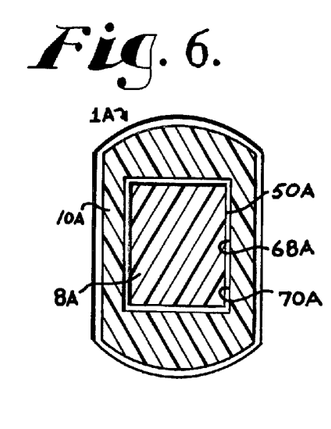
FIG. 6 is an enlarged cross-sectional view, similar to FIG. 3, showing a second embodiment of a dynamic fixation connecting member assembly according to the invention.

FIGS. 6-10 illustrate respective connecting member assemblies 1A, 1B, 1C, 1D and 1E that are identical or substantially similar to the assembly 1 with the exception of the outer dimension of the respective inner core and the inner through bore dimension of the respective slidingly mated sleeve. Unlike the assembly 1 that has a circular cross-section as shown in FIG. 3, the assemblies 1A, 1B, 1C, 1D and 1E have other cross-sectional shapes. In particular, FIG. 6 illustrates the assembly 1A that includes an inner core 8A and an outer sleeve 10A. The core 8A is substantially uniformly rectangular in cross-section, having four planar outer surfaces 50A. The outer sleeve 10A has four cooperating inner surfaces 68A that form a through bore 70A sized and shaped to closely receive the inner core 8A.

Figure 7:
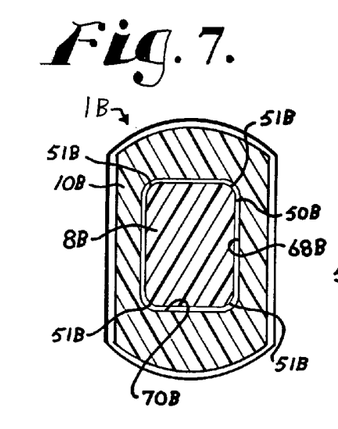
FIG. 7 is an enlarged cross-sectional view, similar to FIG. 3, showing a third embodiment of a dynamic fixation connecting member assembly according to the invention.

FIG. 7 illustrates the assembly 1B that includes an inner core 8B and an outer sleeve 10B. The core 8B is substantially uniformly rectangular in cross-section, having four planar outer surfaces 50B that intersect with one another at curved or rounded corners 51B. The outer sleeve 10B has four cooperating inner surfaces 68B that form a through bore 70B sized and shaped to closely receive the inner core 8A. The bore 70B is of rectangular cross-section and also has rounded corners to receive the rounded corners 51B of the inner core 8B.

Figure 8:
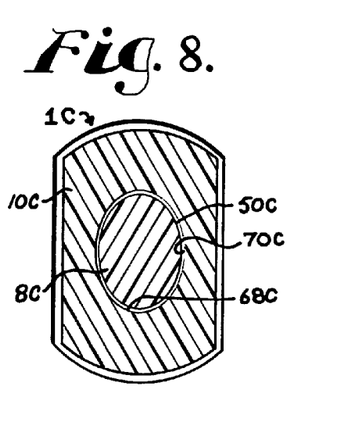
FIG. 8 is an enlarged cross-sectional view, similar to FIG. 3, showing a fourth embodiment of a dynamic fixation connecting member assembly according to the invention.

FIG. 8 illustrates the assembly 1C that includes an inner core 8C and an outer sleeve 10C. The core 8C is substantially uniformly oval or ellipsoidal in cross-section, having a curved outer surface 50C. The outer sleeve 10A has a cooperating curved inner surface 68C that forms a through bore 70C sized and shaped to closely receive the inner core 8C.

Figure 9:
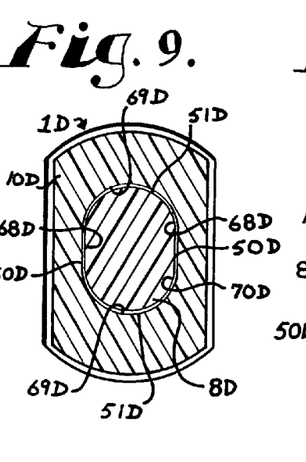
FIG. 9 is an enlarged cross-sectional view, similar to FIG. 3, showing a fifth embodiment of a dynamic fixation connecting member assembly according to the invention.

FIG. 9 illustrates the assembly 1D that includes an inner core 8D and an outer sleeve 10D. The core 8D includes a pair of opposed planar sides 50D and a pair of opposed curved sides 51D. The outer sleeve 10C has a pair of cooperating opposed planar surfaces 68D and a pair of cooperating opposed curved surfaces 69D that form a through bore 70D sized and shaped to closely receive the inner core 8D.

Figure 10:
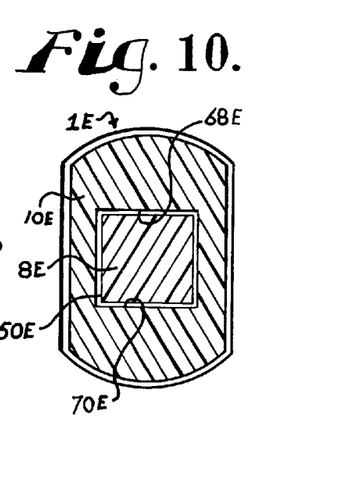
FIG. 10 is an enlarged cross-sectional view, similar to FIG. 3, showing a sixth embodiment of a dynamic fixation connecting member assembly according to the invention.

FIG. 10 illustrates the assembly 1E that includes an inner core 8E and an outer sleeve 10E. The core 8E is substantially uniformly square in cross-section, having four planar outer surfaces 50E. The outer sleeve 10E has four cooperating inner surfaces 68E that form a through bore 70E sized and shaped to closely receive the inner core 8E.

It is to be understood that while certain forms of the present invention have been illustrated and described herein, it is not to be limited to the specific forms or arrangement of parts described and shown.

What is claimed and desired to be secured by Letters Patent is as follows:

1. A medical implant assembly comprising:
   a) first and second bone anchors each having a bone attachment structure on one end and a channel at an opposite end;
   b) an elongate core sized and shaped to be received in the bone anchor channels and extend therebetween;
   c) closures to secure the core in the bone anchor channels; and wherein
   d) the core is pretensioned between the bone anchors so as to elastically elongate while remaining in tension between the bone anchors during usage.

2. The assembly according to claim 1 including an compressible sleeve that surrounds the core, the sleeve positioned between the bone anchors and maintained in compression between both of the bone anchors.

3. The assembly according to claim 1 wherein a bone anchor has a pressure insert that is directly engaged by the core.

4. A medical implant assembly comprising:
   a) first and second polyaxial pedicle screws each having a bone attachment structure on one end and an open channel at an opposite end;
   b) an elongate core sized and shaped to be received in the polyaxial pedicle screw channels and extend entirely therethrough and therebetween;
   c) closures to close and secure the core in the polyaxial pedicle screw channels; and wherein
   d) the core is pretensioned between the polyaxial pedicle screws so as to maintain tension between the polyaxial pedicle screws during usage.

5. The assembly according to claim 1 including an elastic sleeve that surrounds the core that is positioned between the bone anchors and compressively engages both of the bone anchors.

6. The assembly according to claim 1 wherein a bone anchor has a pressure insert that directly engages the core.

7. The assembly according to claim 2, wherein the sleeve engages both of the bone anchors.

8. A medical implant assembly comprising:
   a) first and second bone anchors each having a bone attachment structure on one end and a channel at an opposite end;
   b) an elongate core sized and shaped to be received in the bone anchor channels and extend therebetween;
   c) closures to secure the core in the bone anchor channels; and wherein
   d) the core is pretensioned and elastically stretched between the bone anchors so as to remain in tension and have an elongated stretched length between the bone anchors during usage.

9. The implant according to claim 8, including a sleeve extending between the bone anchors and having a length that is greater than the length of the core between the bone anchor in a non-tensioned state such that the core is stretched to the length of the sleeve during assembly.

\* \* \* \* \*